US009757036B2

(12) United States Patent
Strommer et al.

(10) Patent No.: US 9,757,036 B2
(45) Date of Patent: Sep. 12, 2017

(54) METHOD FOR PRODUCING AN ELECTROPHYSIOLOGICAL MAP OF THE HEART

(71) Applicants:Gera Strommer, Haifa (IL); Uzi Eichler, Hiafa (IL); Liat Schwartz, Haifa (IL); Amit Cohen, Binyamina (IL); Itay Kariv, Haifa (IL)

(72) Inventors: Gera Strommer, Haifa (IL); Uzi Eichler, Hiafa (IL); Liat Schwartz, Haifa (IL); Amit Cohen, Binyamina (IL); Itay Kariv, Haifa (IL)

(73) Assignee: MEDIGUIDE LTD., Haifa (IL)

( * ) Notice: Subject to any disclaimer, the term of this patent is extended or adjusted under 35 U.S.C. 154(b) by 1070 days.

(21) Appl. No.: 13/783,544

(22) Filed: Mar. 4, 2013

(65) Prior Publication Data

US 2013/0184569 A1    Jul. 18, 2013

Related U.S. Application Data

(63) Continuation-in-part of application No. 12/599,225, filed as application No. PCT/IL2008/000656 on May 11, 2008, now Pat. No. 8,706,195.

(Continued)

(51) Int. Cl.
*A61B 5/00* (2006.01)
*A61B 5/06* (2006.01)
(Continued)

(52) U.S. Cl.
CPC .......... *A61B 5/0044* (2013.01); *A61B 5/0075* (2013.01); *A61B 5/0205* (2013.01);
(Continued)

(58) Field of Classification Search
CPC ......... A61B 5/042; A61B 6/503; A61B 19/52; A61B 19/5244; A61B 19/56;
(Continued)

(56) References Cited

U.S. PATENT DOCUMENTS 5,595,183 A    1/1997  Swanson
5,876,336 A    3/1999  Swanson
(Continued)

FOREIGN PATENT DOCUMENTS

WO    2008136008    11/2008

*Primary Examiner* — Amanda Lauritzen Moher
(74) *Attorney, Agent, or Firm* — Dykema Gossett PLLC

(57) ABSTRACT

Methods and systems for producing an electrophysiological map of a heart of a patient are disclosed. An example method may include determining a target location and an orientation of a catheter tip, confirming that the tip is located at the target location, measuring the heart parameter value at each of the target locations, and superimposing a plurality of representations of the heart parameter value. Confirmation that the tip of the catheter is located at a target location can be accomplished by comparing the current location of the tip with the target location, a corresponding heart parameter value being measured at each of the target locations by a heart parameter sensor, and the representations of the heart parameter value being superimposed on an image of the heart at the target location to produce the electrophysiological map.

19 Claims, 18 Drawing Sheets

Related U.S. Application Data

(60) Provisional application No. 60/916,710, filed on May 8, 2007.

(51) Int. Cl.
| | | |
|---|---|---|
| *A61B 8/13* | (2006.01) | |
| *A61B 6/00* | (2006.01) | |
| *A61B 5/042* | (2006.01) | |
| *A61B 8/00* | (2006.01) | |
| *A61B 5/0205* | (2006.01) | |
| *G06F 19/00* | (2011.01) | |
| *A61B 6/03* | (2006.01) | |
| *A61B 8/08* | (2006.01) | |
| *A61B 6/12* | (2006.01) | |

(52) U.S. Cl.
CPC ............. *A61B 5/042* (2013.01); *A61B 5/062* (2013.01); *A61B 5/066* (2013.01); *A61B 5/6852* (2013.01); *A61B 5/72* (2013.01); *A61B 5/743* (2013.01); *A61B 5/7425* (2013.01); *A61B 6/463* (2013.01); *A61B 6/466* (2013.01); *A61B 6/485* (2013.01); *A61B 6/503* (2013.01); *A61B 8/13* (2013.01); *A61B 8/463* (2013.01); *A61B 8/466* (2013.01); *A61B 8/5207* (2013.01); *G06F 19/3437* (2013.01); *A61B 5/0073* (2013.01); *A61B 5/6885* (2013.01); *A61B 6/032* (2013.01); *A61B 6/037* (2013.01); *A61B 6/12* (2013.01); *A61B 6/487* (2013.01); *A61B 6/5205* (2013.01); *A61B 6/5288* (2013.01); *A61B 8/0841* (2013.01); *A61B 8/0883* (2013.01); *A61B 8/483* (2013.01); *A61B 8/5284* (2013.01)

(58) Field of Classification Search
CPC ...... A61B 2019/505; A61B 2019/5251; A61B 2019/5289; A61B 5/04011; A61B 5/7445; A61B 6/504; A61B 5/0044; A61B 5/0073; A61B 5/0075; A61B 5/72; A61B 5/7425; A61B 5/743; A61B 6/032; A61B 6/037; A61B 6/12; A61B 6/463; A61B 6/466; A61B 6/485; A61B 6/487; A61B 6/5205; A61B 6/5288; A61B 8/0841; A61B 8/0883; A61B 8/13
See application file for complete search history.

(56) References Cited

U.S. PATENT DOCUMENTS

| | | |
|---|---|---|
| 6,400,981 B1 | 6/2002 | Govari |
| 6,690,963 B2 | 2/2004 | Ben-Haim |
| 6,716,166 B2 | 4/2004 | Govari |
| 7,720,520 B2 | 5/2010 | Willis |
| 8,180,428 B2 | 5/2012 | Kaiser |
| 8,190,238 B2 | 5/2012 | Moll |
| 2002/0026118 A1 | 2/2002 | Govari |
| 2002/0065455 A1 | 5/2002 | Ben-Haim |
| 2003/0018251 A1 | 1/2003 | Solomon |
| 2003/0158477 A1 | 8/2003 | Panescu |
| 2006/0084884 A1* | 4/2006 | Beatty ................ A61B 5/04085 600/523 |
| 2006/0095022 A1* | 5/2006 | Moll ....................... A61B 8/12 606/1 |
| 2008/0287794 A1* | 11/2008 | Li ............................ A61B 5/06 600/439 |

* cited by examiner

METHOD FOR PRODUCING AN ELECTROPHYSIOLOGICAL MAP OF THE HEART

CROSS-REFERENCE TO RELATED APPLICATIONS

This application is a continuation-in-part of U.S. application Ser. No. 12/599,225, filed 30 Sep. 2010, now pending (the '225 application), which is a national stage filing based upon international application no. PCT/IL2008/000656, filed 11 May 2008, (the '656 application), which claims priority to U.S. application Ser. No. 60/916,710, filed 8 May 2007, (the '710 application). The '225 application, the '656 application, and the '710 application are all hereby incorporated by reference in their entirety as though fully set forth herein.

BACKGROUND a. Field of the Invention

The present disclosure relates to medical devices in general, and to methods and systems for producing an electrophysiological map, in particular.

b. Background Art

Cardiac arrhythmia is a well known medical condition where the regular beating rhythm of the heart is disrupted. These disruptions are caused by disturbances in the propagation path of electrical impulses in the myocardial tissue. These disturbances are caused, for example, by ischemia to a region in the myocardial tissue. Thus, the propagation of electrical impulses, through the myocardial tissue, may slow down. These ischemic regions create patterns of circular propagation of electric impulses. This circular propagation pattern disrupts the normal propagation pattern of electrical impulse, thus, causing irregular activation of the atria or ventricle. As a further example, cardiac arrhythmias are also caused by anatomical obstacles (e.g., dead tissue). These obstacles cause electric impulses to propagate around the obstacles, thus, disrupting the normal propagation of impulses to the atria or ventricular.

These conditions may be treated with an ablation procedure. During this procedure, a physician inserts an ablation catheter to the region of interest where abnormal propagation of electric impulses occurs, and ablates that region. This ablation is performed by using, for example, heat, electromagnetic pulses or cryogenic fluid.

Abnormal propagation pathways are found by an electrophysiology study procedure of the heart. During this procedure, a physician typically inserts an electrode or electrodes into or near the heart. During the arrhythmia electrodes measure the electric potential at different locations in the heart. Using this information, an electric potential map of the heart is formed, identifying regions of interest.

U.S. Patent Application Publication No. 2003/0158477 to Panescu and entitled "Systems and Methods for Guiding Catheters Using Registered Images", is directed to a system for producing a three-dimensional volume of the heart. The system includes a mapping catheter, a registration processor, a plurality of fiducials, and an external imaging device. The mapping catheter includes a plurality of mapping elements at its tip. The fiducials are attached to the chest of the patient. The fiducials which show up on an image of the heart, can be used to register an externally acquired image with a three-dimensional coordinate system.

U.S. Pat. No. 5,595,183 to Swanson et al., entitled "Systems and Methods for Examining Heart Tissue Employing Multiple Electrode Structures and Roving Electrodes" (Swanson et al. '183), is directed to a system and a method for pacing and mapping the heart for the diagnosis and treatment of cardiac conditions. Swanson et al. '183 is directed to a system including a mapping probe and an ablation probe. The mapping probe carries a three dimensional multiple electrode structure which takes the form of a basket. This basket structure is formed by splines extending from a base member (i.e., where the splines are connected to the catheter) to an end cap (i.e., where the splines are connected together). These splines are made from Nitinol metal or silicone rubber. A plurality of electrodes, are positioned on each of these splines. These electrodes are operative as either sensors or sources of electrical energy at the point of contact with the myocardial tissue.

The Swanson system operates in two modes, the sampling mode and the matching mode. In the sampling mode, the basket structure is deployed in the desired region of the heart. An electrode or pairs of electrodes are activated to produce electrical energy to the myocardial tissue pacing the heart. The electrodes then record electrograms. In the matching mode, the system compares the resulting paced electrogram morphologies to a plurality of electrogram morphology templates collected during the sampling mode. Based upon this comparison, the system generates an output that identifies the location of an electrode or electrodes on the basket structure that are close to a possible ablation site. An ablation catheter is then inserted for ablating the site.

U.S. Pat. No. 5,876,336 to Swanson et al., entitled "Systems and Methods for Guiding Movable Electrode Elements Within Multiple Electrode Structure" (Swanson et al. '336), is directed to a method and a system for remotely locating electrode elements at precise locations within the body of a patient. The system in Swanson et al. '336 includes a mapping probe and an ablation probe. The mapping probe carries a three dimensional multiple electrode structure which takes the form of a basket. This basket structure is formed by splines extending from a base member to an end cap. These splines are made from Nitinol metal or silicone rubber. A plurality of electrodes is positioned on each of these splines. These electrodes sense electrical activity in heart tissue. The sensed electrical activity is processed to create a map of this electrical activity. A physician uses this map to identify regions for possible ablation.

Once a region is selected for ablation, an ablation probe (i.e., ablation catheter), including an ablation electrode, is inserted to the heart and placed in contact with the tissue in the selected region. The ablation electrode emits ablation energy (e.g., heat or electromagnetic energy) to the contacted heart tissue to destroy that tissue.

The '336 system includes a processing unit for guiding the ablation catheter. This processing unit determines the position of the ablation catheter within the space defined by the basket structure in terms of the relative position of the electrodes on the basket splines. First, the position of the ablation of the catheter in a horizontal sector, between adjacent horizontal sets of electrodes is determined. This horizontal sector is determined by sensing the phase difference between the phase of an oscillator signal, sequentially applied to each set of electrodes and the phase of the ablation electrode. If the ablation catheter is beneath the electrode set, the phase difference sign is negative. If the ablation catheter is above the electrode set, the phase difference sign is positive.

Next, an arcuate sector symmetrically bisected by a spline is determined. This arcuate sector is determined using differential amplitude sensing or differential phase sensing between the ablation electrode and a spline, to which an oscillating signal is applied. The arcuate sector, bisected by the spline yielding the smallest amplitude difference or the smallest phase difference, is selected. The bisection of the horizontal sector with the arcuate sector forms a pie shaped sector. The position of the ablation catheter in the pie shaped sector is determined according to the distance of the ablation catheter from the basket electrodes. The closer the ablation catheter is to the electrodes, the higher the peak voltage sensed from these electrodes. Thus, the distance from the electrodes is determined according to the sensed peak voltage during the determination of the arcuate sector.

U.S. Pat. No. 6,400,981 to Govari, entitled "Rapid Mapping of Electrical Activity in the Heart," is directed to a method for mapping electrical potentials inside a volume. In Govari, a mapping catheter, including a plurality of electrodes is inserted into a chamber of the heart, to generate a map of the electrical activity over an endocardial surface of the heart. These electrodes are distributed over the surface of the distal part of the catheter. The catheter further includes at least one position sensor at the distal part of the catheter. A geometrical model of the endocardial surface is formed by the catheter. Electrical potentials are measured within the volume of the chamber using the electrodes on the catheter. Since the position of the electrodes with respect to the position sensor is known, the measured potentials are combined with the geometrical model, thus generating a map of the electrical potentials at the endocardial surface.

BRIEF SUMMARY

It is desirable to be able to provide a novel method and system for producing an electrophysiological map of a heart of the body of a patient. In accordance with the present invention, there is thus provided a method and a system for producing an electrophysiological map of a heart of the body of a patient.

In accordance with the disclosed technique, there is thus provided a method for producing an electrophysiological map of a heart of the body of a patient. The method includes the procedures of determining a respective target point location, and a probe orientation, confirming that the tip of a probe catheter is located at the target point location, and confirming that the tip is oriented at the probe orientation. The method further includes the procedures of measuring the heart parameter value at each of the respective target point locations, and superimposing a plurality of representations respective of the heart parameter value.

The target point location, and probe orientation, are determined with respect to a heart parameter value, which is to be measured, for each of a plurality of target points within the heart. It is confirmed that the tip of a probe catheter is located at the respective target point location, by comparing the currently detected location of the tip, with the respective target point location. It is confirmed that the tip is oriented at the respective probe orientation, by comparing the currently detected orientation of the tip, with the respective probe orientation. The heart parameter value at each of the respective target point locations is measured by a heart parameter sensor located at the tip. The representations respective of the heart parameter value are superimposed on an image of the heart, at the respective target point location, to produce the electrophysiological map.

In accordance with another aspect of the disclosed technique, there is thus provided a method for producing an electrophysiological map of the heart. The method includes the procedures of registering a medical positioning system (MPS) with an image detector, navigating a probe catheter to a plurality of points within a heart chamber of the heart, and detecting a heart parameter at each of the points. The method further includes the procedures of determining the position at each of the points, associating each of the heart parameters with a respective one of the positions, and constructing an electrophysiological map of the heart chamber, according to a plurality of pairs of the heart parameters and the respective positions.

The MPS is registered with an image detector, wherein the image detector detects the image of the heart. The probe catheter is navigated to a plurality of points within the heart chamber, according to a representation of the position of an electrophysiological probe located at the tip of the probe catheter, in the image. The probe catheter includes an MPS sensor in the vicinity of the electrophysiological probe. The MPS sensor is coupled with the MPS. The MPS sensor detects the position. The heart parameter is detected at each of the points, by the electrophysiological probe. The position at each of the points is determined according to an output of the MPS sensor. An electrophysiological map of the heart chamber is constructed, according to a plurality of pairs of the heart parameters and the respective positions.

An exemplary method for producing an electrophysiological map of a heart in accordance with another embodiment includes reconstructing a three-dimensional model of the heart from a plurality of two-dimensional images, wherein a coordinate system of the three-dimensional model is registered with a medical positioning system coordinate system. The method further includes for each of a plurality of target points within the heart, determining a respective target point location associated with the three-dimensional model and a respective target probe orientation at which a heart parameter value is to be measured. The method still further includes for each target point, confirming that a probe of a catheter is located at the respective target point location by comparing a currently detected location of the probe with the respective target point location; confirming that the probe is oriented at the respective probe orientation by comparing the currently detected orientation of the probe with the respective target probe orientation; measuring the heart parameter value with a heart parameter sensor; and producing the electrophysiological map.

In another embodiment, a system for producing an electrophysiological map of a heart of a patient includes an organ monitor, configured to determine an activity state of a heart, and a medical positioning system coupled with the organ monitor and associated with a medical positioning coordinate system configured to determine the current position of a catheter according to an output of a medical positioning sensor. The system further includes a two-dimensional image detector associated with a three-dimensional coordinate system pre-registered with the medical positioning coordinate system, the two-dimensional image detector configured to acquire a plurality of two-dimensional images and associate each two-dimensional image with a position in the three-dimensional coordinate system, a position in the medical positioning coordinate system, and the activity state of the heart. The system still further includes a heart parameter measurement unit configured to measure at least one heart parameter value at a target position, each heart parameter value being associated with a position in the medical positioning coordinate system. The system still further includes a processor configured to receive data and to construct a three-dimensional model of the heart according to the two-dimensional images, superimpose a representation of the current position of the catheter on the three-dimensional model, confirm that the catheter is positioned at the target location, produce an electrophysiological map, direct a display to display the superimposed three-dimensional model according to a real-time activity state of the heart as detected by the organ monitor.

The foregoing and other aspects, features, details, utilities, and advantages of the present invention will be apparent from reading the following description and claims, and from reviewing the accompanying drawings.

DETAILED DESCRIPTION

Figure 1A:
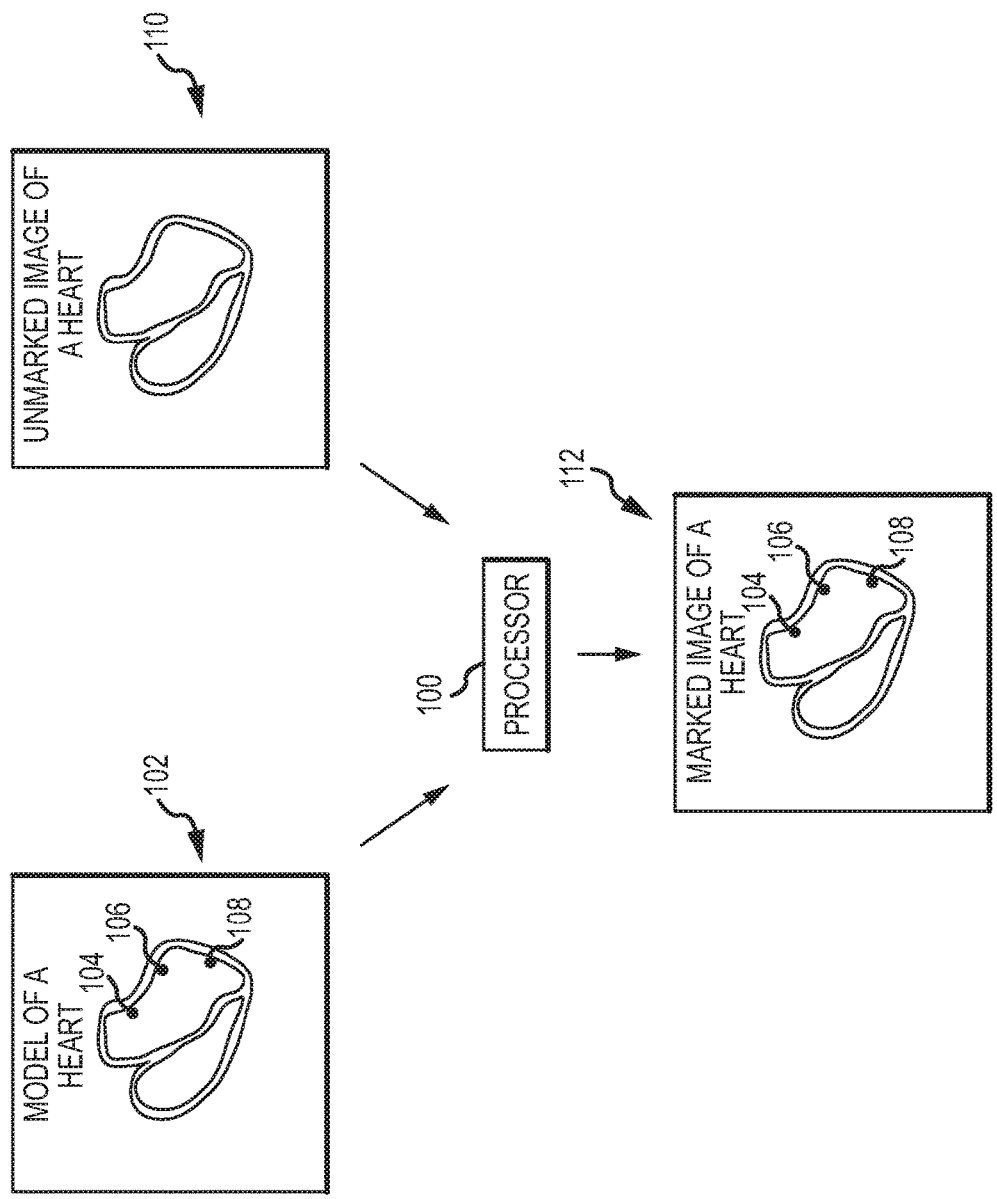
FIG. 1A is a schematic illustration of a marked image of a heart of the body of a patient, produced according to an embodiment of the present invention.

The disclosed technique overcomes the disadvantages of the prior art by employing a probe catheter to mark a plurality of strategic points on an image of the heart and measuring the electric potential of the heart at each one of these points, after confirming that the tip of the probe catheter is located and oriented at each point properly relative to the surface of the tissue of the heart. A medical positioning system (MPS) and an MPS sensor located at the tip of the probe catheter can be employed for determining the location and orientation of the tip of the catheter. Since an MPS coordinate system of the MPS is registered with an image coordinate system of the image of the heart (either three-dimensional (3D) or two-dimensional (2D)), a processor can superimpose a representation of the value of each of the electric potential measurements, on the strategic points on the image of the heart, to produce an electrophysiological map.

Additionally, a potentiometer can be coupled with the probe catheter to measure a change in electric potential at each point due to a stimulated pulse at the coronary sinus of the heart, and measuring the local activation time (LAT). In this manner an LAT map of the heart can be constructed. An electrocardiogram (ECG) can be employed for compensating for the movements of the heart during contractions. In this manner a still image of the heart can be displayed in order to facilitate marking the points on the image of the heart despite the movements of the heart.

The term "heart parameter" herein below refers to a parameter specific to the heart such as electric potential and LAT, and/or any other relevant organ information, such as activation timing, voltage maps, propagation, impedance and the like. The term "tomographic image detector," refers to an image detector which acquires a plurality of 2D images from different sections of an organ of a patient. The tomographic image detector can be a computed tomography (CT), magnetic resonance imager (MRI), positron emission tomography (PET), single photon emission computer tomography (SPECT), ultrasound image detector, infrared image detector, X-ray imager, and the like. The tomographic image detector can produce a 3D image of the organ by reconstructing the 2D images. In other words, a tomographic image detector can detect a 3D image of an organ by first acquiring a plurality of 2D images or slices of the organ and then reconstructing those 2D slices into the 3D image. The tomographic image detector can acquire the images either prior to the operation (i.e., preoperative image detector), such as CT, MRI, PET, SPECT, or in real-time (i.e., real-time image detector), as in the case of ultrasound, infrared and X-ray.

The term "2D image detector" herein below, refers to an image detector which acquires a two-dimensional image of the organ, such as fluoroscope, ultrasound, and the like. In the description herein below, the term "image detector" interchangeably refers to a tomographic image detector, as well as a 2D image detector. The coordinate system associated with the image detector may be pre-registered with the MPS coordinate system. Thus, the coordinate system associated with each image acquired by the image detector is also pre-registered with the MPS coordinate system. The term "position" herein below, refers either to the location, to the orientation or both the location and the orientation, of an object in a three-dimensional coordinate system.

Figure 1B:
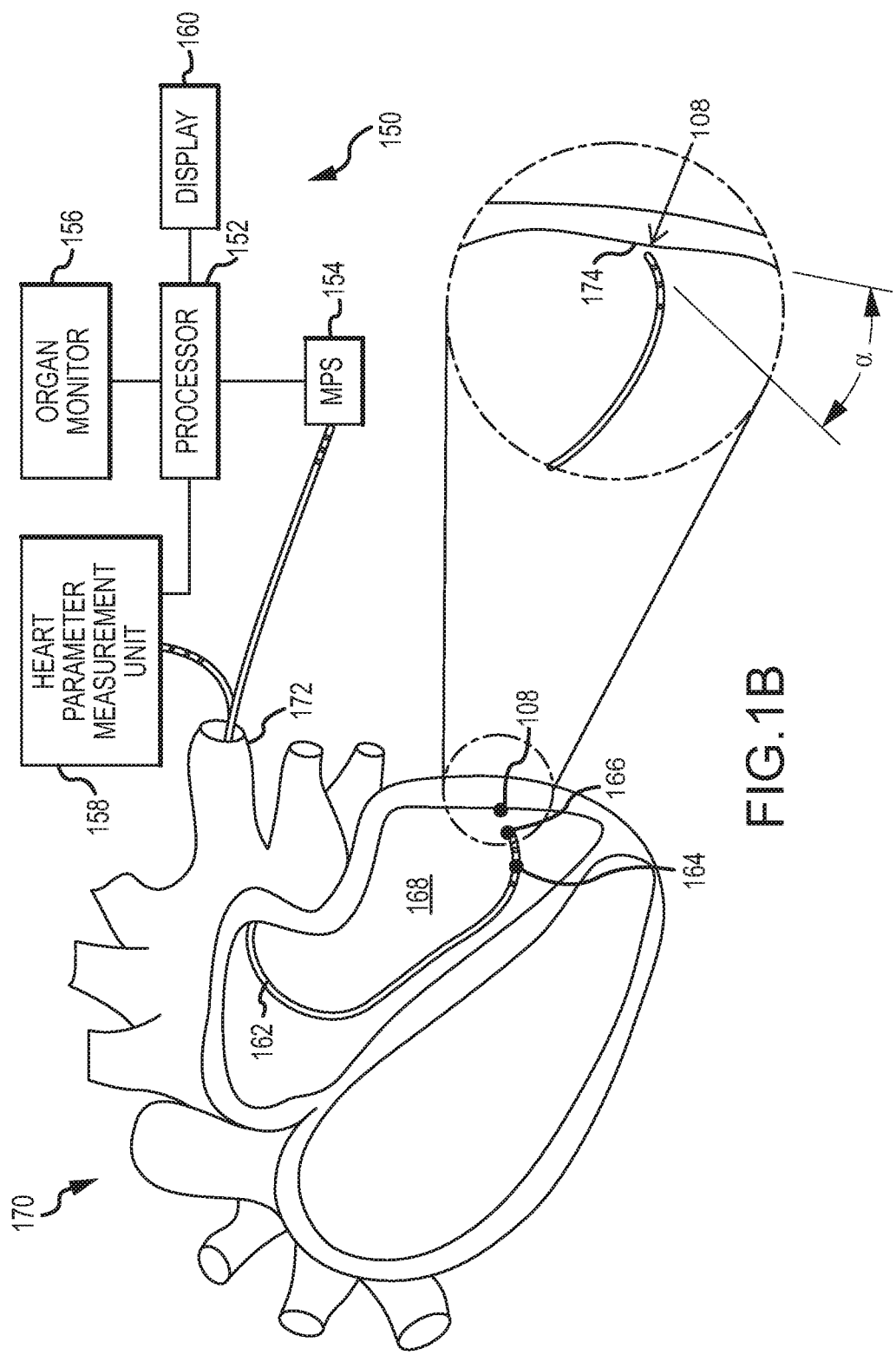
FIG. 1B is a schematic illustration of a system for measuring a heart parameter after confirming that the tip of a probe catheter is located at a target point in the marked image of FIG. 1A, and oriented at a predetermined orientation, constructed and operative according to a further embodiment of the present invention.

Reference is now made to FIGS. 1A, and 1B. FIG. 1A is a schematic illustration of a marked image of a heart of the body of a patient 112 produced according to an embodiment of the disclosed technique. FIG. 1B is a schematic illustration of a system 150 for measuring a heart parameter after confirming that the tip of a probe catheter is located at a target point in the marked image of FIG. 1A, and oriented at a predetermined orientation, constructed and operative according to a further embodiment of the disclosed technique.

With reference to FIG. 1A, a processor 100 receives data respective of a model 102 of a representative heart. Model 102 includes data respective of the location of a plurality of target points 104, 106, and 108, within the representative heart. Each of target points 104, 106, and 108, is defined as a point within a typical heart, at which an electrophysiological parameter is to be measured. An image detector (not shown), acquires an unmarked image 110 of a heart. Processor 100 registers unmarked image 110 with model 102 and produces marked image 112 by superimposing target points 104, 106, and 108 on unmarked image 110. Alternatively, a surgeon (not shown) can direct processor 100 to produce marked image 112 by manually marking target points 104, 106, and 108 on unmarked image 110 via a user interface (not shown), for example, based on the symptoms of the patient, a previous diagnosis of the patient, and the like.

With reference to FIG. 1B, system 150 includes a processor 152, an MPS 154, an organ monitor 156, a heart parameter measurement unit 158, a display 160, and a probe catheter 162. Probe catheter 162 includes an MPS sensor 164 and a heart parameter sensor 166 at a tip. Processor 152 is coupled with MPS 154, organ monitor 156, heart parameter measurement unit 158, and with display 160. MPS sensor 164 is coupled with MPS 154. Heart parameter sensor 166 is coupled with heart parameter measurement unit 158.

Organ monitor 156 is a device which detects an organ timing signal of a patient's organ, such as the ECG of the heart, or a respiration signal of the lungs. MPS 154 is a device which determines the position of MPS sensor 164 (i.e., the position of the tip of probe catheter 162), according to an output of MPS sensor 164, which MPS sensor 164 produces in response to an electromagnetic field. Additionally, instead of MPS 154, other position detectors known in the art, such as sonar, optical, and the like, can be employed. Such position detectors may comprise conventional apparatus known generally in the art, for example, an EnSite™ Velocity™ system having EnSite™ NAVX™ software functionality, commercially available from St. Jude Medical, Inc. and as generally shown with reference to commonly assigned U.S. Pat. No. 7,263,397 entitled "Method and Apparatus for Catheter Navigation and Location and Mapping in the Heart," the entire disclosure of which is incorporated herein by reference or other known technologies for locating/navigating a catheter in space (and for visualization), including for example, the CARTO visualization and location system of Biosense Webster, Inc., (e.g., as exemplified by U.S. Pat. No. 6,690,963 entitled "System for Determining the Location and Orientation of an Invasive Medical Instrument" hereby incorporated by reference), the AURORA® system of Northern Digital Inc, or a hybrid magnetic field-impedance based system, such as the CARTO 3 visualization and location system of Biosense Webster, Inc. (e.g., as exemplified by U.S. Pat. No. 7,536, 218, hereby incorporated by reference).

Processor 152 directs display 160 to display marked image 112 (FIG. 1A). Marked image 112 is a previously acquired image of a heart 170 on which a plurality of target points, such as target point 108, are superimposed. Processor 152 can direct display 160 to display marked image 112, according to a real-time organ timing signal of heart 170. Hence, it is not necessary to expose the patient and a surgeon to the ionizing radiation (e.g., X-rays) of the image detector while performing the medical operation on the patient. The surgeon enters probe catheter 162 into a left ventricle 168 of heart 170 through a pulmonary vein 172 or other vessels, which may be more suitable than the pulmonary vein 172. MPS 154 determines the current position of the tip of probe catheter 162, according to an output of MPS sensor 164. Processor 152 produces a superimposed image of heart 170 by superimposing a representation of the position of the tip of probe catheter 162 on marked image 112. Hence, the surgeon is able to observe a real-time representation of the tip of probe catheter 162 as the surgeon navigates probe catheter 162 within left ventricle 168.

When using a measurement by heart parameter measurement unit 158 to measure a heart parameter it is confirmed that the tip of probe catheter 162 is located at target point 108 (i.e., target point location), and that preferably the tip of probe catheter 162 is oriented at a predetermined orientation relative to a surface 174 (e.g., an angle α). It is preferred that for heart parameter sensor 166 to detect a reliable value of the heart parameter, the value of angle α has to be within a predetermined range of angles. This is due to the fact that a reading of heart parameter sensor 166 depends on the orientation of heart parameter sensor 166 at point of contact with the tissue of left ventricle 168.

The surgeon can visually confirm the location of the tip of probe catheter 162 by observing an image of a radiopaque marker (not shown), located at the tip of probe catheter 162, on a real-time image (not shown) of heart 170 (e.g., a fluoroscope). Alternatively, the surgeon can confirm the location of the tip of probe catheter 162 by observing the representation of the tip of probe catheter 162 which processor 152 produces according to an output of MPS 154. On the other hand, the orientation of the tip of probe catheter 162 can also be confirmed only using the output of MPS 154. Further alternatively, instead of the confirmation by the surgeon, the processor can direct a user interface (not shown) coupled therewith, to notify the surgeon that the tip of the probe catheter is located at the target point, and is oriented at the predetermined orientation by producing an aural or visual output. Alternatively, instead of a manual navigation by the surgeon an automatic navigation system coupled with the processor can be employed for automatically maneuvering and navigating the probe catheter within the body of the patient and within the left ventricle according to a previously acquired topological map of the circulation system of the body of the patient.

After confirming the location and orientation of the tip of probe catheter 162 processor, 152 directs heart parameter measurement unit 158 to measure the heart parameter at target point 108 according to the output of heart parameter sensor 166. Heart parameter measurement unit 158 measures the heart parameter at additional target points such as target points 104 and 106 (FIG. 1A). Processor 152 produces an electrophysiological map (not shown) of heart 170 by interpolating between the individual heart parameter values, and directs display 160 to display this electrophysiological map.

Figure 2:
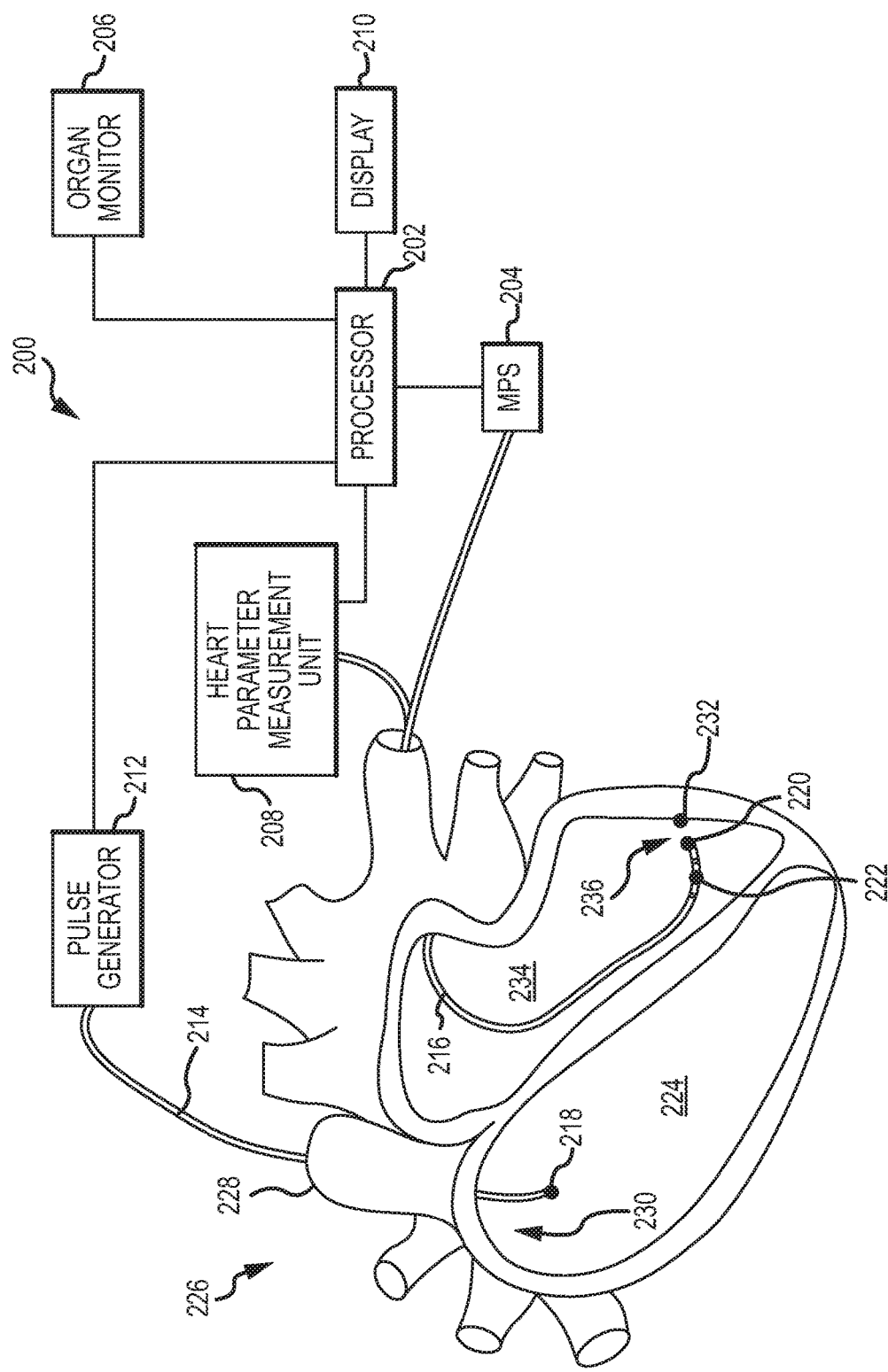
FIG. 2 is a schematic illustration of a system for measuring a heart parameter of a heart of the body of a patient, constructed and operative according to yet a further embodiment of the present invention.

Reference is now made to FIG. 2, which is a schematic illustration of a system generally referenced 200, for measuring a heart parameter of a heart of the body of a patient, constructed and operative according to a further embodiment of the disclosed technique. System 200 includes a processor 202, an MPS 204, an organ monitor 206, a heart parameter measurement unit 208, a display 210, a pulse generator 212, a stimulation catheter 214, and a probe catheter 216. Stimulation catheter 214 includes an electrode 218 at the tip thereof. Probe catheter 216 includes a heart parameter sensor 220 and an MPS sensor 222, at the tip thereof.

Processor 202 is coupled with MPS 204, organ monitor 206, heart parameter measurement unit 208, display 210, and with pulse generator 212. Electrode 218 is coupled with pulse generator 212. Heart parameter sensor 220 is coupled with heart parameter measurement unit 208. MPS sensor 222 is coupled with MPS 204.

The surgeon enters stimulation catheter 214 into a right ventricle 224 of a heart 226 of the body of a patient (not shown) through a superior vena cava 228 of heart 226 and maintains electrode 218 at a sinoatrial node 230 of heart 226. The surgeon positions the tip of probe catheter 216 at a target point 232 in a left ventricle 234 of heart 226, as described herein above in connection with FIGS. 1A and 1B.

Processor 202 directs pulse generator 212 to produce an electric pulse at electrode 218. This electric pulse travels within right ventricle 224 and left ventricle 234 substantially similar to the way a pulse produced by sinoatrial node 230 would travel within right ventricle 224 and left ventricle 234. Heart parameter sensor 220 constantly senses the electric potential at target point 232. Once the electric pulse produced by electrode 218 reaches a region 236 of left ventricle 234, heart parameter sensor 220 senses an electric potential differential and produces an output, accordingly. Heart parameter measurement unit 208 determines the value of this electric potential differential, according to the output of heart parameter sensor 220.

Processor 202 determines the time interval (i.e., local activation time—LAT) between the moment pulse generator 212 produces the electric pulse, and the moment heart parameter sensor 220 senses the electric potential differential. Processor 202 determines additional values of LAT at other target points within heart 226 while electrode 218 is maintained at sinoatrial node 230 and probe catheter 216 is moved to other target points within heart 226. Processor 202 produces an LAT map of heart 226, similar to the way system 150 (FIG. 1B) produces an electrophysiological map of heart 170, as described herein above. Processor 202 directs display 210 to display this LAT map of heart 226.

Figure 3:
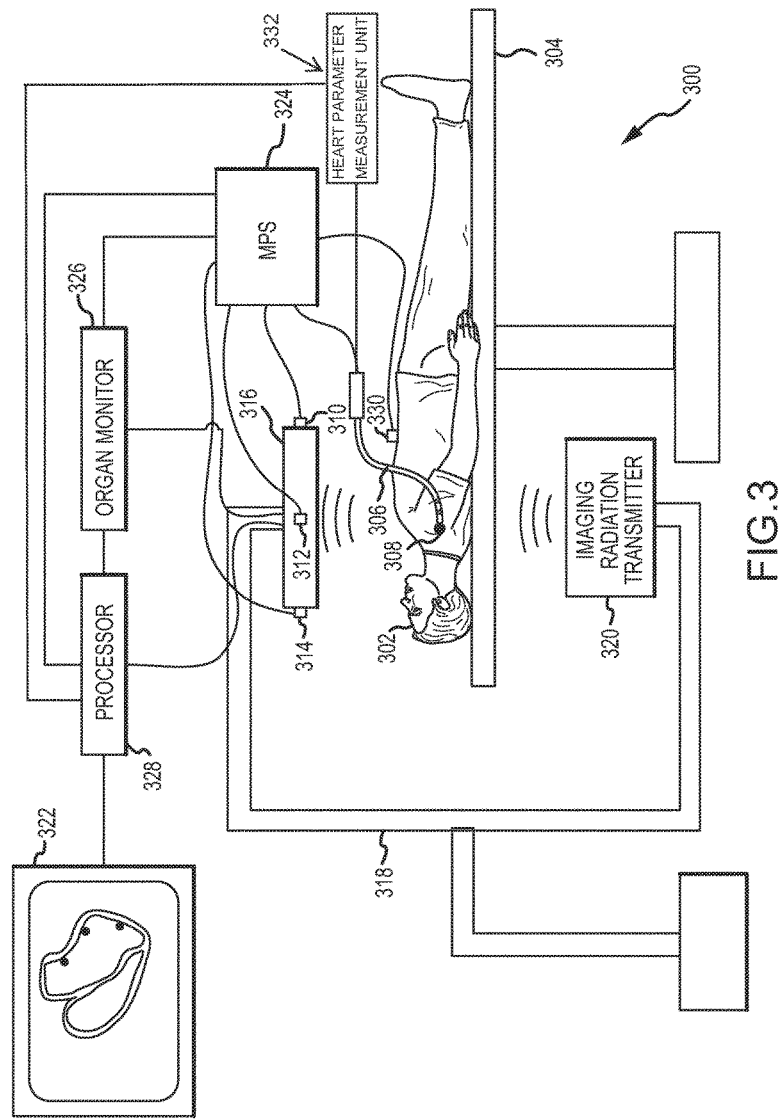
FIG. 3 is a schematic illustration of a system for reconstructing a 3D representation of the heart constructed and operative in accordance with yet a further embodiment.

Reference is now made to FIG. 3, which is a schematic illustration of a system 300 for reconstructing a 3D representation of the heart, generally referenced 300, constructed and operative in accordance with another embodiment of the disclosed technique. System 300 includes medical 2D image detector 318 associated with a respective 3D coordinate system, an MPS 324 associated with a respective MPS coordinate system, an organ monitor 326, a processor 328, a catheter 306, a display unit 322 and a table 304. System 300 further includes a heart parameter measurement unit 332. 2D image detector 318 includes an imaging radiation transmitter 320 and an imaging radiation detector 316. MPS 324 includes MPS transmitters 310, 312 and 314, reference sensor 330 and an MPS sensor (not shown). The heart parameter measurement unit 332 is coupled to at least one heart parameter sensor located on the catheter 306.

Processor 328 is coupled with organ monitor 326, with imaging radiation detector 316, with MPS 324, with the heart parameter measurement unit and with display unit 322. MPS 324 is further coupled with organ monitor 326 and with catheter 306 and with the heart parameter measurement unit 332. The MPS sensor and the heart parameter sensor are coupled with distal tip 308 of catheter 306. Heart parameter measurement unit is further coupled with organ monitor 326. Organ monitor 326 is further coupled with 2D image detector 318. In the example set forth in FIG. 3, MPS transmitters 310, 312 and 314 are fixed to imaging radiation detector 316. Consequently, the coordinate system associated with 2D image detector 318 is pre-registered with the MPS coordinate system.

Alternatively, when the transmitters are not fixed to the image detector (e.g., located under table 304), the coordinate system associated with the 2D image detector 318 can be pre-registered with the MPS coordinate system by employing an optical-magnetic calibration procedure prior to or during the use of system 300. This optical-magnetic calibration includes, for example, attaching another MPS sensor (not shown) to radiation detector 316. Thus, the position of radiation detector 316 and each image acquired thereby can be determined in the MPS coordinate system. According to another example, optical-magnetic calibration includes positioning fiducial markers at known positions in the MPS coordinates system. Representations of these fiducial markers are visible in the images acquired by medical 2D image detector 318. Thus, processor 328 can determine the locations of these fiducial markers in the coordinate system associated with the 2D image detector 318. Accordingly, processor 328 determines a transformation between the MPS coordinate system and the coordinate system associated with the 2D image detector 318.

2D image detector 318 acquires a plurality of 2D images. Each image is associated with a respective different position (i.e., location and orientation) in the 3D coordinate system associated with 2D image detector 318, for example, by rotating around patient 302. Since the 3D coordinate system of 2D image detector 318 is registered with the MPS coordinate system, each acquired 2D image is also associated with a respective position in the MPS coordinate system. 2D image detector 318 provides the acquired images to processor 328. Processor 328 reconstructs a 3D model of the organ according to the acquired 2D images and the respective locations thereof. Thus, the coordinate system of the reconstructed 3D model is also registered with the MPS coordinate system. In other words, the 3D model is reconstructed in registration with the MPS coordinate system. Consequently, the need to register the coordinate system of the 3D reconstructed model with the MPS coordinate system is alleviated.

In general, the heart moves in cyclic motion according to the cardiac cycle. The cardiac cycle includes a plurality of cardiac activity states. To account for this motion, system 300 may reconstruct a 3D model for each cardiac activity state. Accordingly, 2D image detector 318 acquires a plurality of 2D images. Each image is associated with a respective position in the coordinate system of the 2D image detector 318 and with a respective cardiac activity state of the heart determined according to an organ timing signal reading acquired by organ monitor 326. Processor 328 groups the 2D images exhibiting substantially the same organ timing signal reading, and reconstructs a 3D model of the organ for each activity state according to the group of 2D images associated with substantially the same activity state. Thus, each 3D model is associated with a respective activity state. Processor 328 may then direct display 322 to display the reconstructed 3D model exhibiting substantially the same respective activity state as a real-time activity state (i.e., also detected by organ timing signal monitor 326). Alternatively, processor 328 may reconstruct a single 3D model of the heart (i.e., as described above) and direct display 322 to display this 3D model at a plurality of different locations on display 322, each location corresponding to the activity states of the heart, according to a real-time organ timing signal (i.e., the 3D model moves in synchronization with the real-time detected activity state of the heart).

Organ monitor 326 is, for example, an ECG monitor. According to another example, organ monitor 326 is a unit which determines the cardiac activity state of the heart. Organ monitor 326 may determine the respiratory activity state as well as the cardiac activity state. Organ monitor 326 may determine the activity state of the heart according to the positions of an MPS sensor located within the heart (e.g., at the coronary sinus) thereby providing data related to the actual motion of the heart (e.g., due to both the cardiac and respiratory cycles). In some embodiments, a plurality of 3D models of the patient's heart can be generated, each representing a different cardiac phase. The system 300 may then generate an electrophysiology map from these 3D models to ascertain additional information such as, for example, the 3D geometrical dynamics associated with the heart over a period of time.

After reconstructing the 3D model, processor 328 directs display 322 to display the reconstructed 3D model. The surgeon may then mark selected points on the 3D model. Similar to that described above, the surgeon enters catheter 306 into a left atrium of the heart, for example, using a transseptal puncturing technique. MPS 324 determines the current position of the tip of catheter 306, according to an output of the MPS sensor. Processor 328 produces a superimposed image of the heart, by superimposing a representation of the position of the tip of catheter 306, on the marked image. Hence, the surgeon is able to observe a real-time representation of the tip of catheter 306, as the surgeon navigates catheter 306 within the left atrium.

Before directing the heart parameter measurement unit 332 to measure a heart parameter, processor 328 confirms that the tip of catheter 306 is located at a selected target point. Furthermore, processor 328 confirms that the tip of catheter 306 is oriented at a predetermined orientation relative to the surface of the left ventricle. Processor 328 confirms that the tip of catheter 306 is located and oriented correctly according to the position (i.e., location and orientation) of the MPS sensor located on catheter 306. After confirming the location and orientation of the tip of catheter 306, processor 328 directs the heart parameter measurement unit 332 to measure the heart parameter at the selected target point. At least some of these steps are repeated and after measuring the heart parameter at a plurality of target points, processor 328 produces an electrophysiological map (not shown) of the heart according to the measured heart parameter values and the respective measurement positions. For example, processor 328 may color the three-dimensional image of the heart according to the measured heart parameters (e.g., where each color represents a voltage) at the locations in the three-dimensional image corresponding to the locations of measurement.

A situation may occur when the point of contact of the tip with the wall of the heart does not match the target point location, due to discrepancies between the 3D image or model of the heart, displayed to the user, and the actual geometry of the heart. These discrepancies may occur, for example, due to the time elapsed between the acquisition of the 3D model or image and the treatment. As a result of these discrepancies, the electrophysiology map of the heart may be inaccurate. To overcome the inaccuracy caused by the discrepancies between the 3D image or model of the heart and the actual geometry of the heart, a contact determining module (not shown), which for example, may be included in processor 328, can determine when the tip of catheter 306 makes contact with the wall of the heart. In at least one embodiment, processor 328 determines when the tip 308 of catheter 306 contacts the wall of the heart according to a pressure sensor (not shown) located at the tip 308 of catheter 306. Thus, when catheter 306 makes contact with the heart wall, the pressure on the tip 308 increases. When the pressure exceeds a pre-specified threshold the processor 328 calculates that catheter 306 made contact with the wall of the heart. Alternatively, processor 328 may determine that the tip 308 of catheter 306 made contact with the wall of the heart when the measurement of a heart parameter (e.g., voltage) exceeds a threshold. According to yet another alternative embodiment, processor 328 may determine that the tip of catheter 306 made contact with the wall of the heart by analyzing a real-time fluoroscopic or ultrasound image, which includes a representation of the tip of the catheter and of the wall of the heart. According to a further alternative embodiment, processor 328 may determine when the tip 308 of catheter 306 made contact with the wall of the heart by detecting irregularities in the movement of the tip of the catheter (e.g., irregular deceleration of the tip of the catheter or irregular orientations of the tip of the catheter). Processor 328 can determine these irregularities in the movement of the tip 308 of the catheter 306 according to the position readings of the tip 308 of the catheter provided by MPS 324 and the time at which these readings are acquired. According to yet a further alternative embodiment, processor 328 may determine when the tip 308 of catheter 306 made contact with the wall of the heart according to any combination of the embodiments mentioned above. With one or more of the various embodiments described above, the user of the system may manually indicate and/or verify contact with the heart wall.

After or contemporaneous with determining that the tip 308 of catheter 306 made contact with the wall, MPS 324 determines the position of the tip 308 of catheter 306 according to the output of the MPS sensor. Processor 328 maps the position of the tip 308 of catheter 306, at the point of contact, to a corresponding position on the 3D model, as further explained below.

According to another aspect of the disclosed technique, the surgeon navigates a probe catheter to a plurality of known points within a heart chamber (i.e., also known as the cardiac chamber) of the heart of the patient, by visually observing a probe heart parameter sensor of the probe catheter and a representation of the position of the probe sensor, at these known points, in respective images of the heart chamber. The probe catheter includes an MPS sensor close to the probe heart parameter sensor. The MPS which is coupled with the MPS sensor is registered with the coordinate system of the image detector which detects a three-dimensional image of the heart chamber. Therefore, the processor can determine the position of the probe at each of these points and associate it with a respective heart parameter detected by the probe. In this manner, the processor can construct an electrophysiological map of the heart chamber. The three-dimensional image can be a computerized tomography generated image which defines the inner surface of the cardiac heart chamber. The surgeon maneuvers the probe to known points on that inner surface, the MPS sensor confirms arrival at these known points and the probe measures a desired parameter (e.g., electric potential, temperature, pressure) at each of these points. After gathering enough information, the processor can generate a map of this parameter on the inner surface.

Figure 4A:
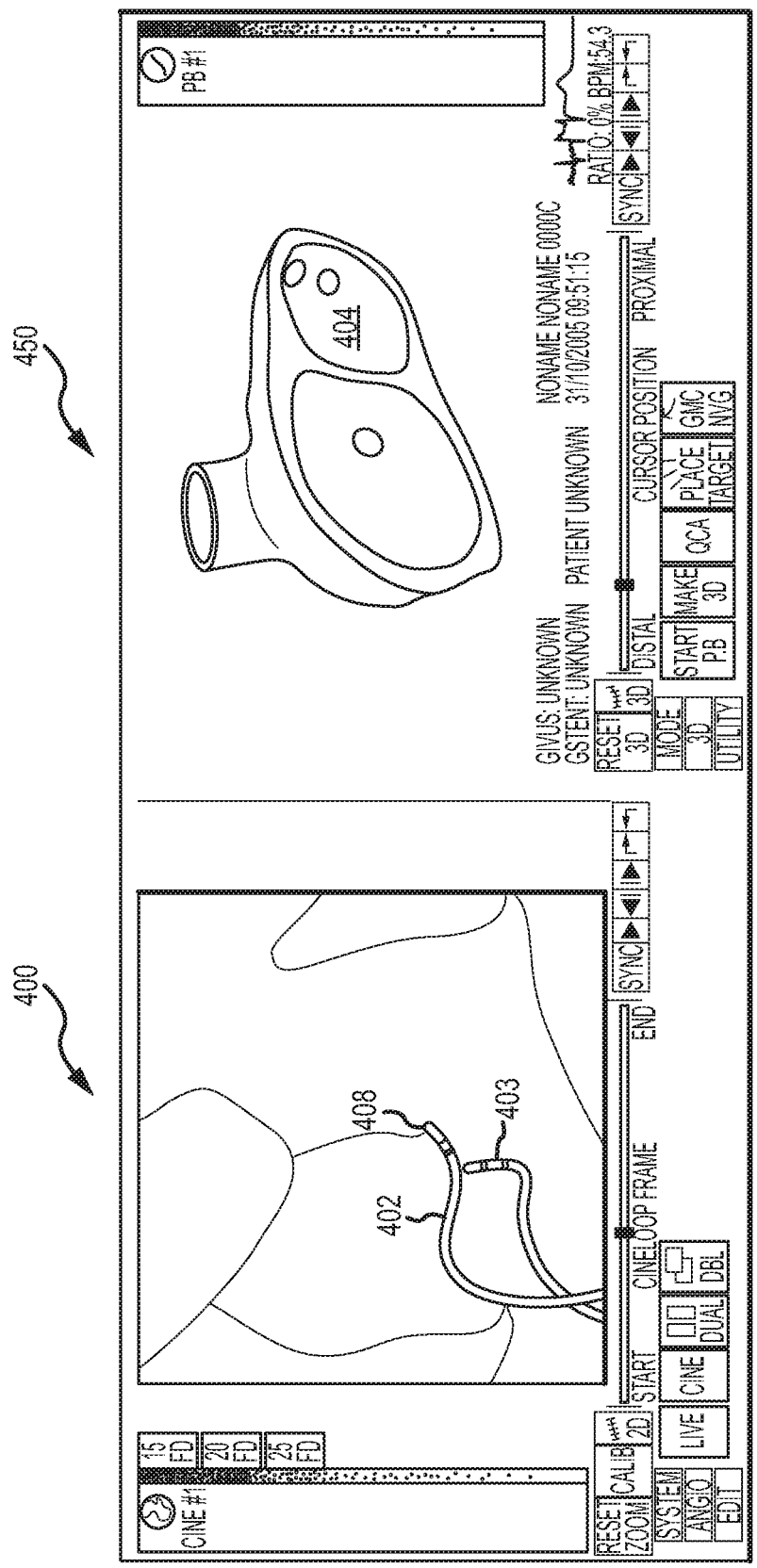
FIG. 4A is a schematic illustration of a graphical user interface (GUI) including a real-time two-dimensional image of the heart chamber of the heart of the body of a patient, and a previously acquired three-dimensional image of the heart chamber, at a stage prior to registration of an MPS with an image detector detecting the two-dimensional image, constructed and operative according to yet a further embodiment of the present invention.
Figure 4B:
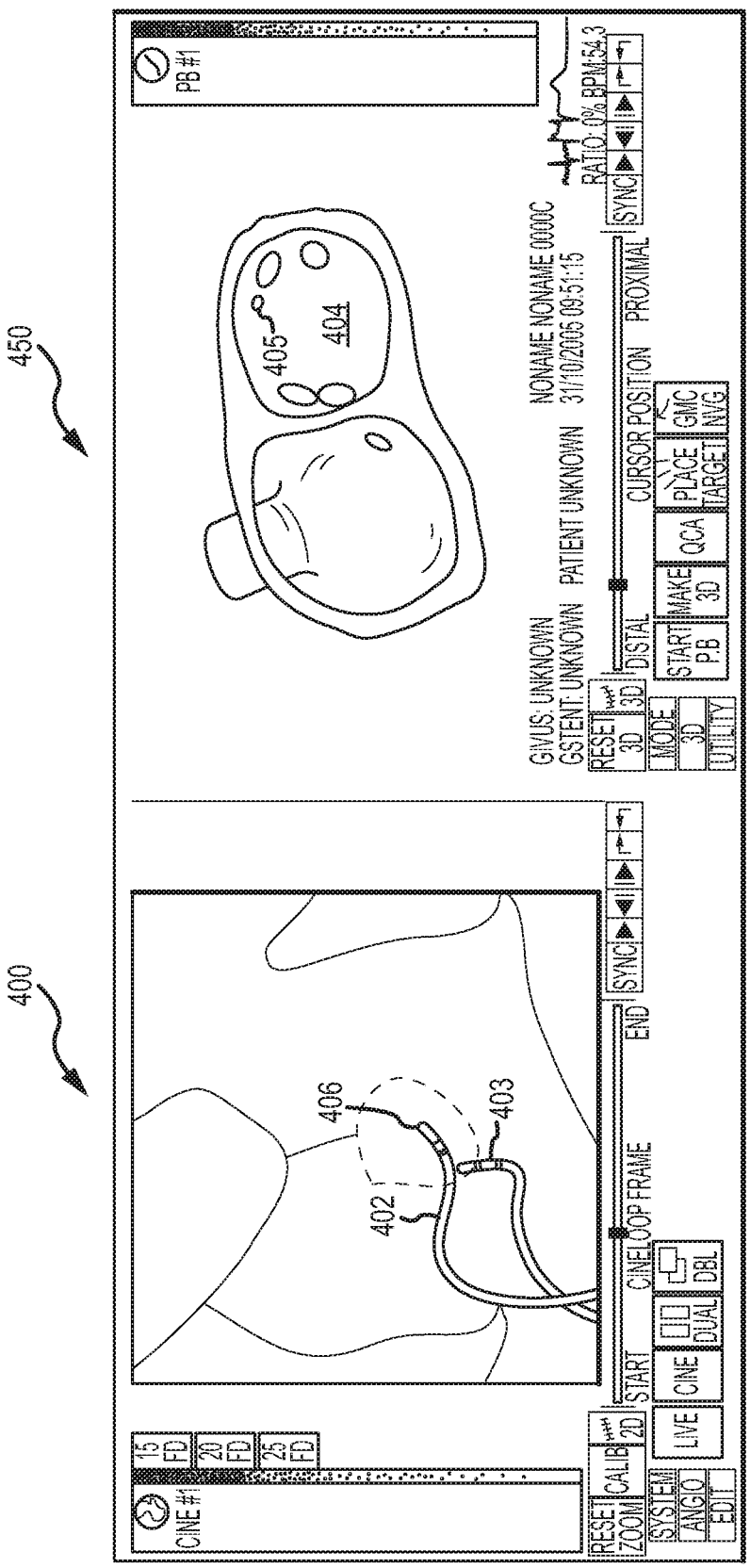
FIG. 4B is a schematic illustration of the GUI of FIG. 4A, during registration of the MPS with the image detector.
Figure 4C:
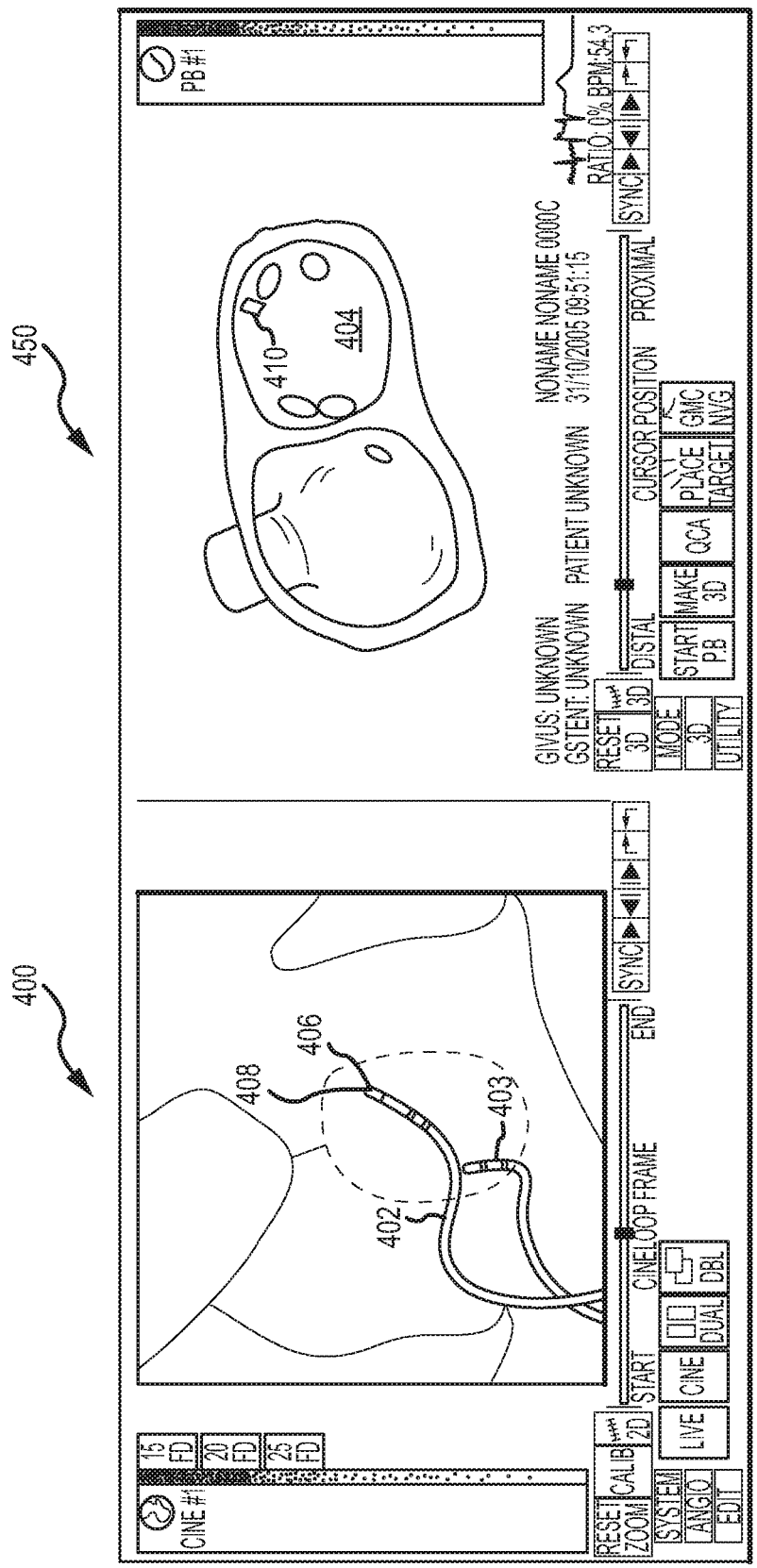
FIG. 4C is a schematic illustration of the GUI of FIG. 4A, during navigation of a probe catheter within the heart chamber.
Figure 4D:
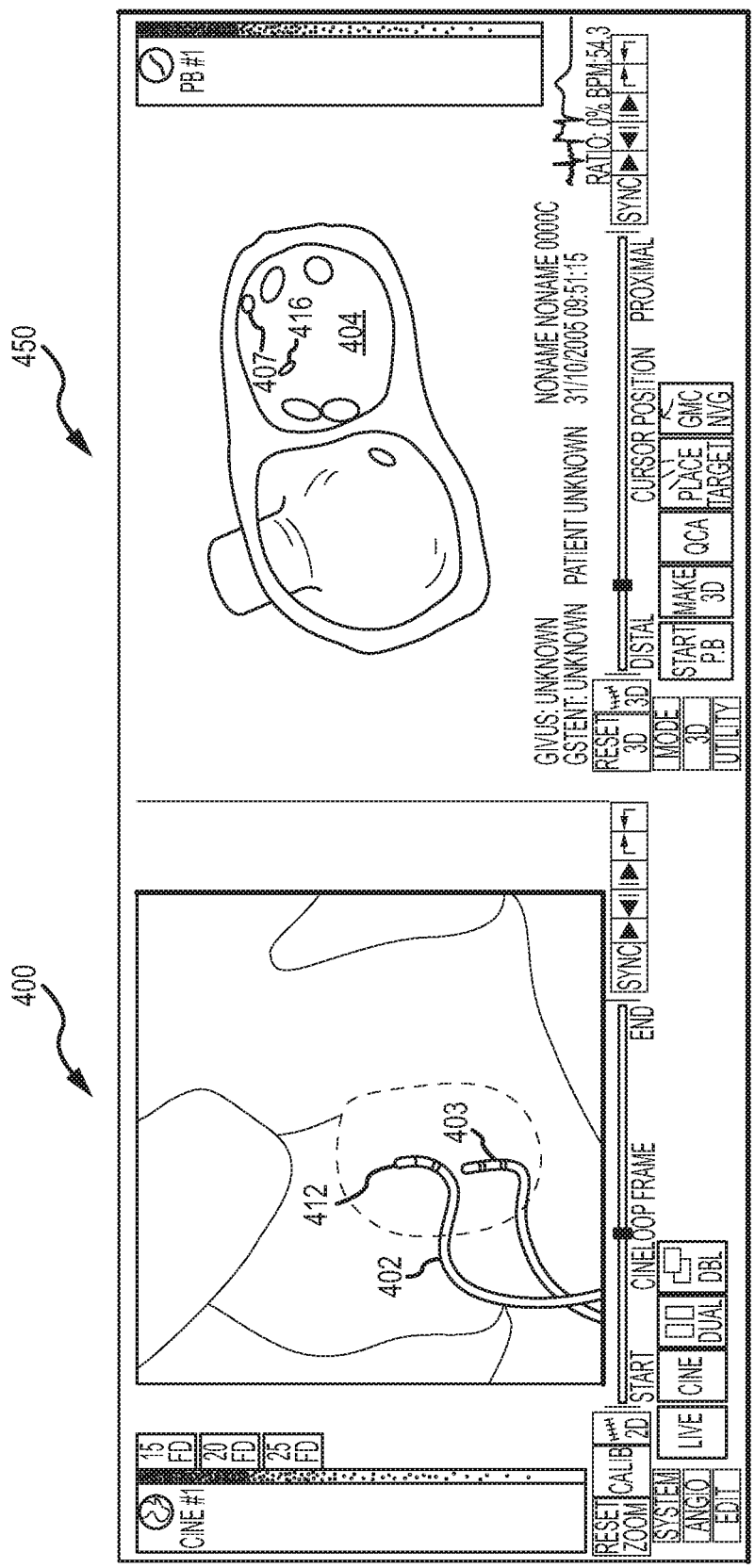
FIG. 4D is a schematic illustration of the GUI of FIG. 4C, during further navigation of the probe catheter of FIG. 4C, to another point within the heart chamber.
Figure 4E:
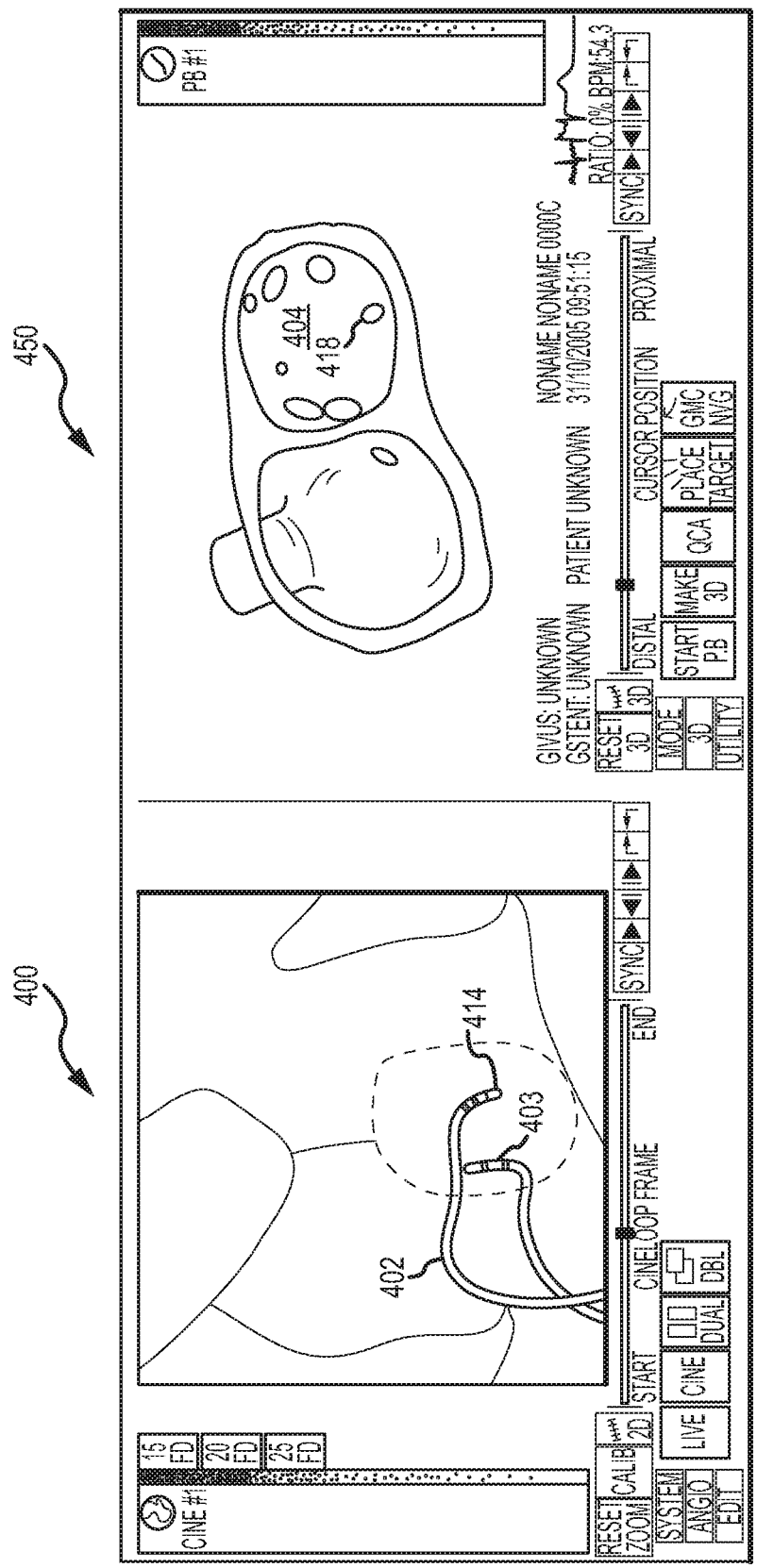
FIG. 4E is a schematic illustration of the GUI of FIG. 4C, during navigation of the probe of FIG. 4C, to a further point within the heart chamber.
Figure 4F:
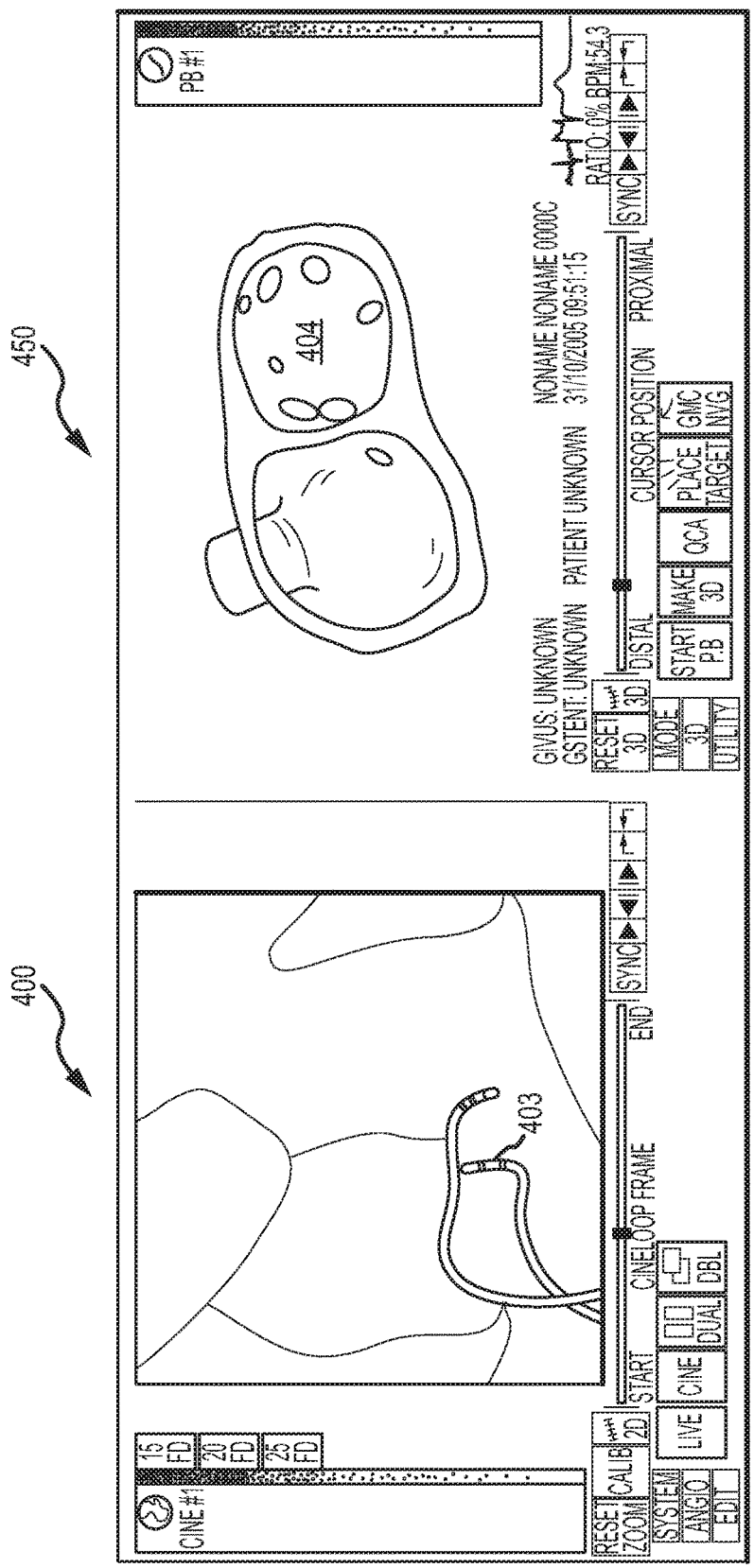
FIG. 4F is a schematic illustration of the GUI including a two-dimensional real-time image of the heart chamber, and a previously acquired three-dimensional image of the heart chamber, including an electrophysiological map the heart chamber, constructed and operative according to a further embodiment of the disclosed technique.
Figure 4G:
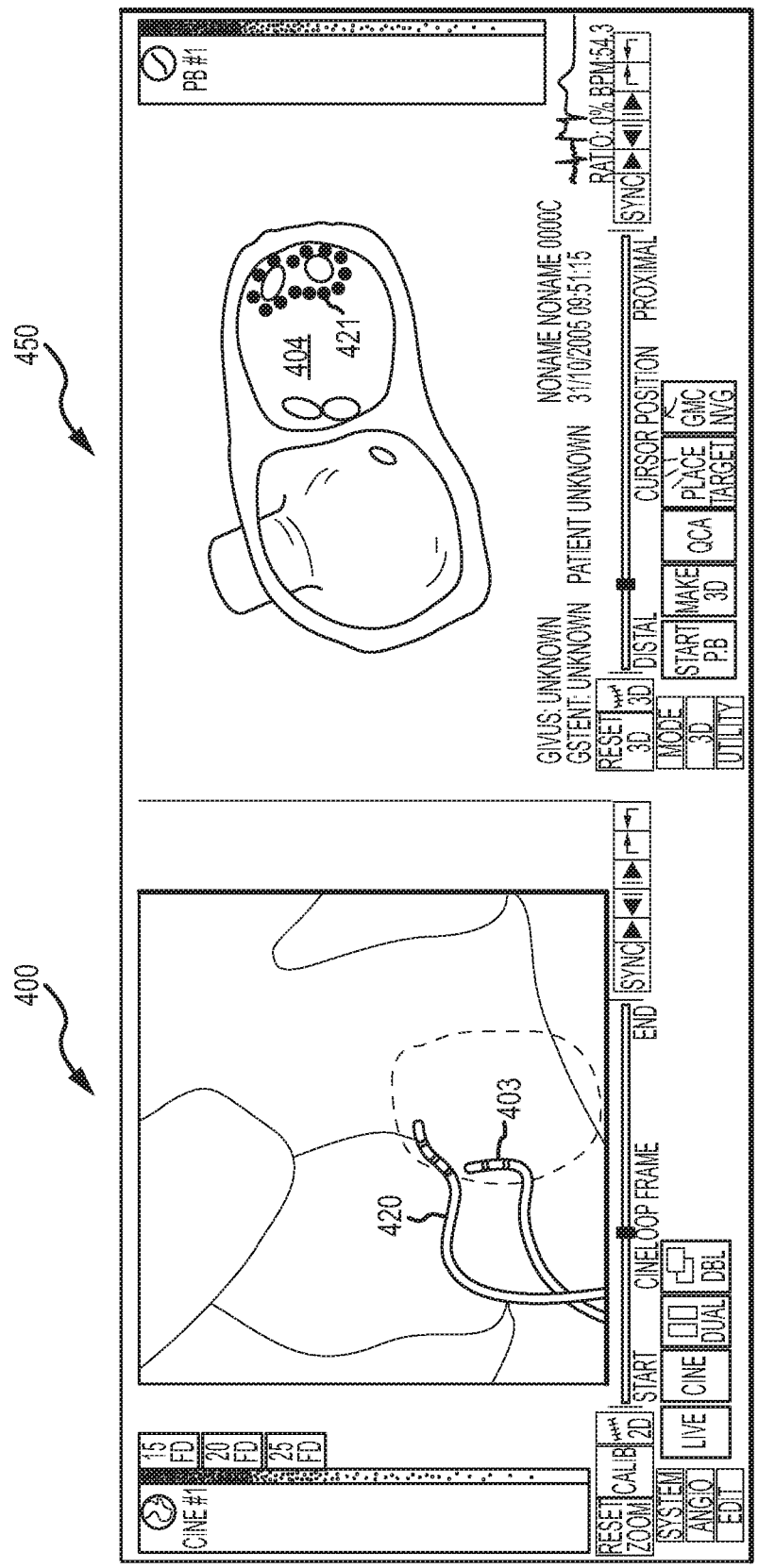
FIG. 4G is a schematic illustration of the GUI of FIG. 4F, during ablation of a region of a pulmonary vein of the heart of the patient.
Figure 4H:
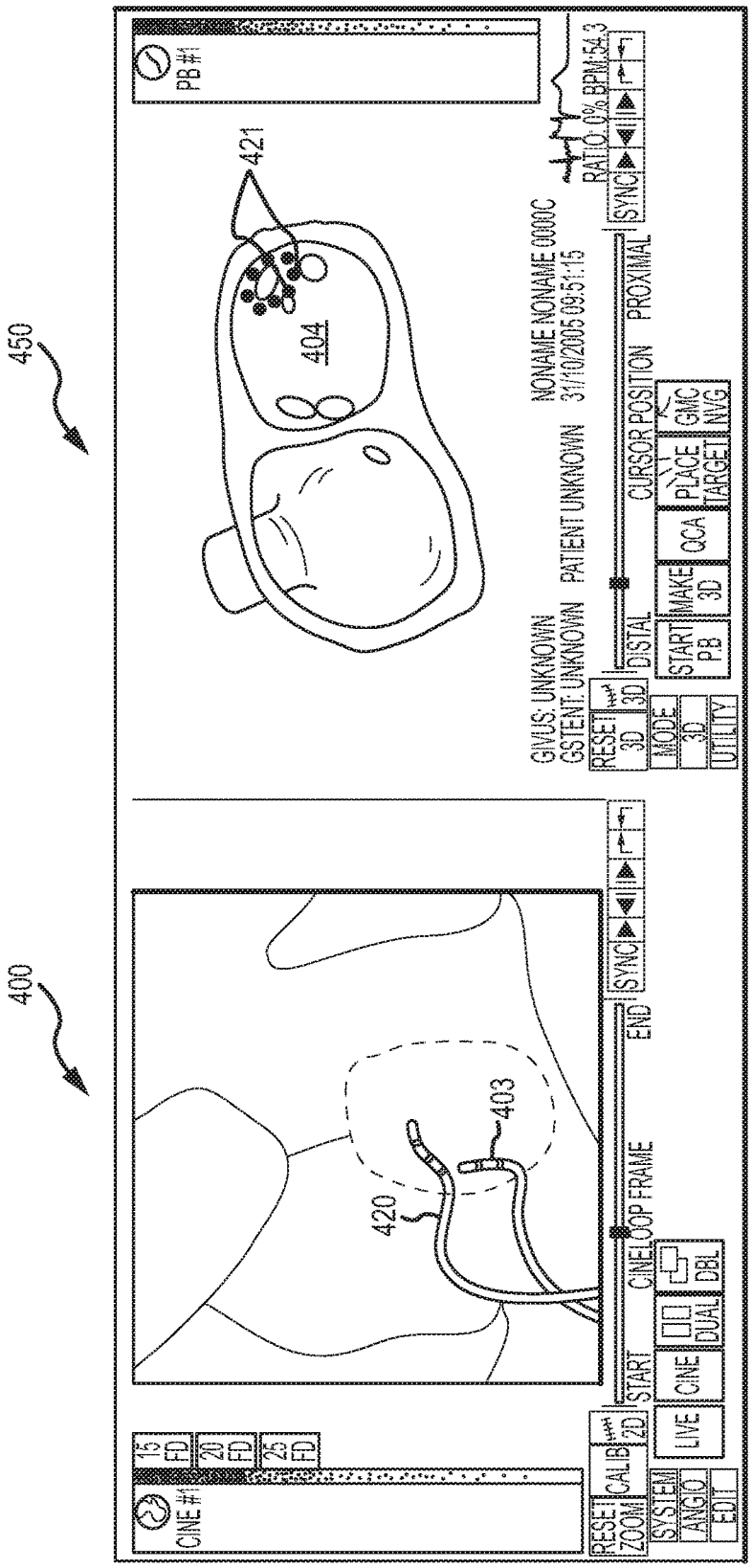
FIG. 4H is a schematic illustration of the GUI of FIG. 4F, during ablation of another region of the pulmonary vein of the heart.
Figure 4I:
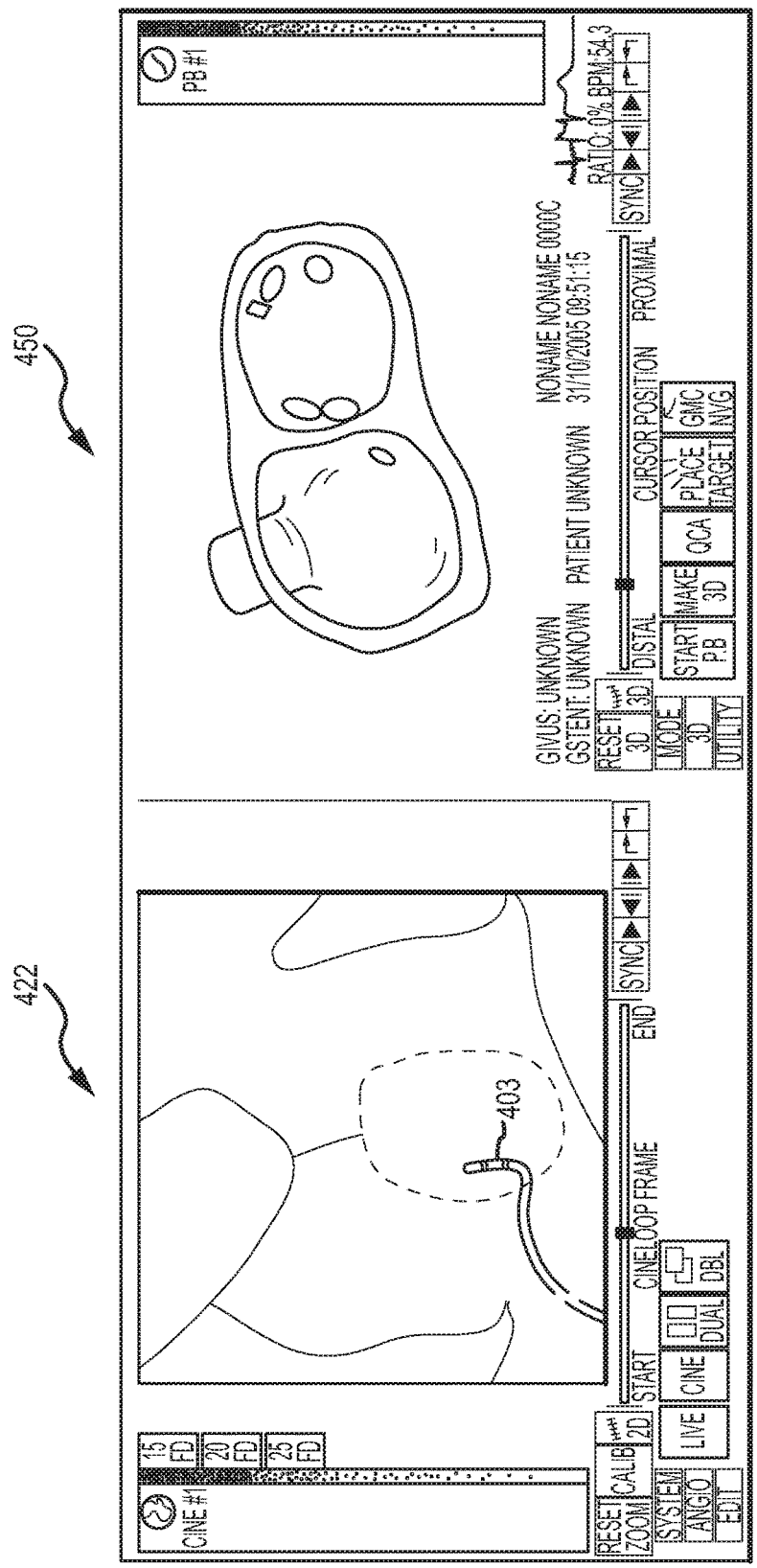
FIG. 4I is a schematic illustration of a GUI including a previously acquired two-dimensional image of the heart chamber, and a previously acquired three-dimensional image of the heart chamber, constructed and operative according to another embodiment of the disclosed technique, during navigation of the probe catheter to a point within the heart chamber.
Figure 4J:
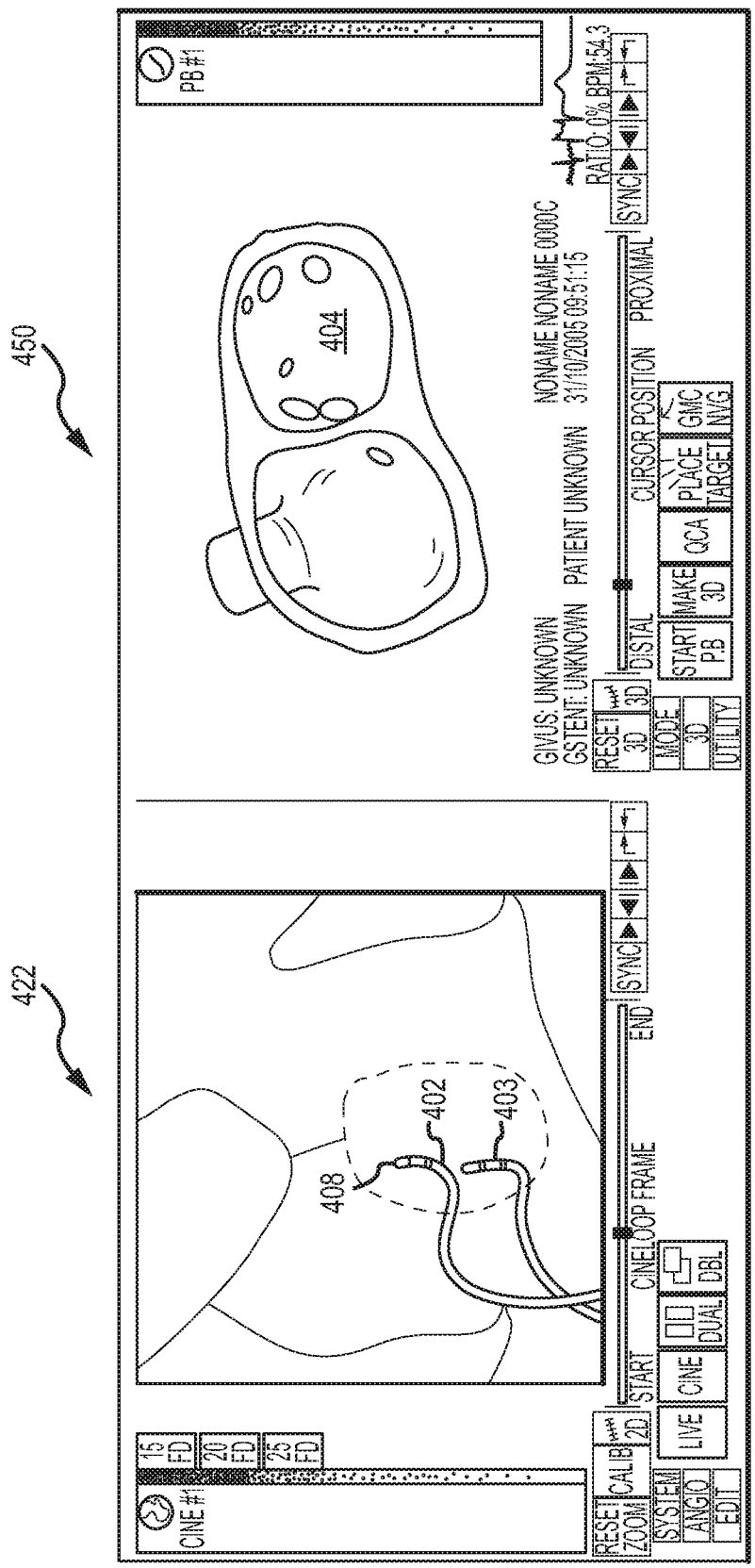
FIG. 4J is a schematic illustration of the GUI of FIG. 4I, during navigation to another point within the heart chamber.
Figure 4K:
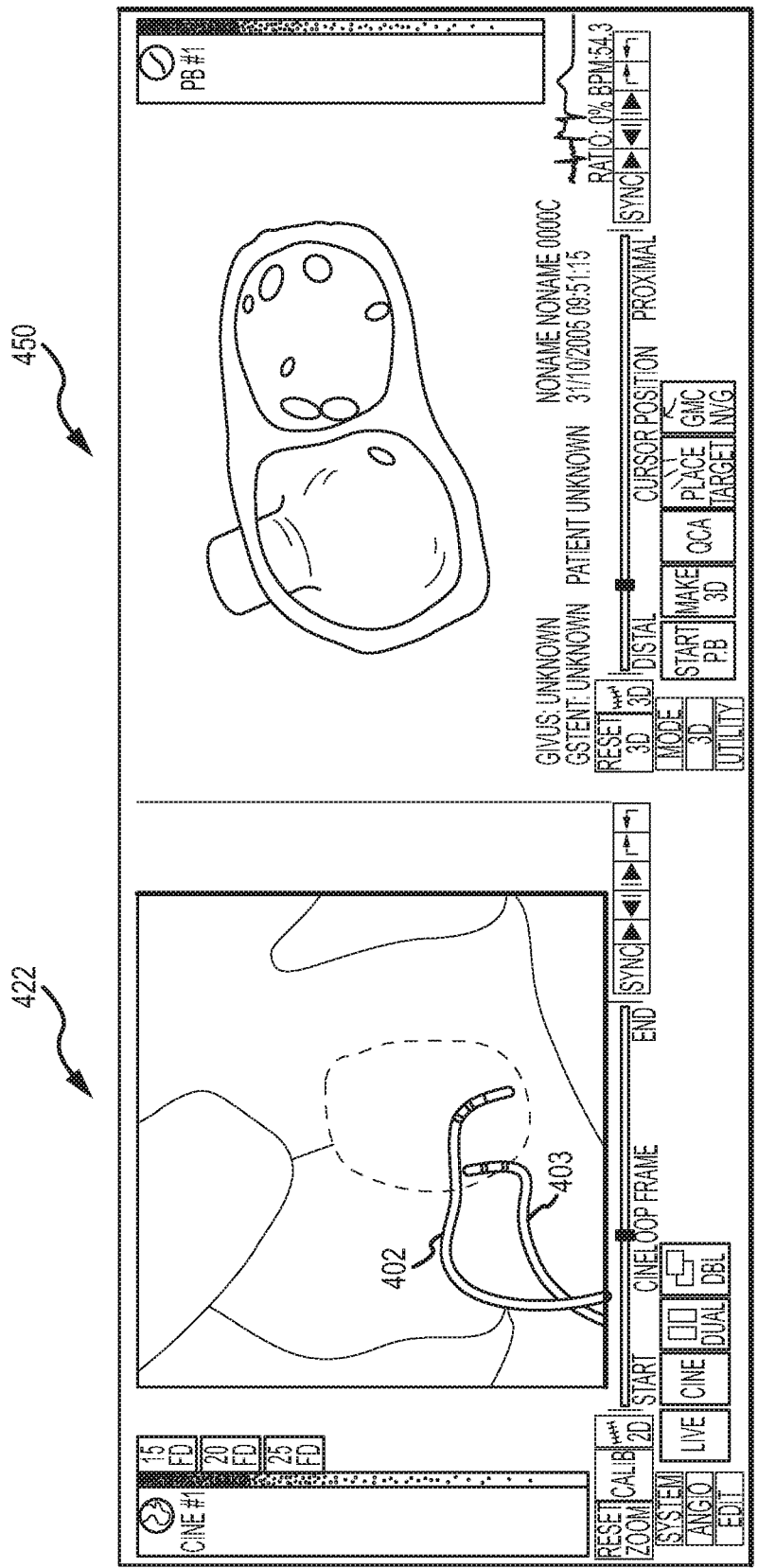
FIG. 4K is a schematic illustration of the GUI of FIG. 4I, during navigation to a further point within the heart chamber.

Reference is now made to FIGS. 4A, 4B, 4C, 4D, 4E, 4F, 4G, 4H, 4I, 4J, and 4K. FIG. 4A is a schematic illustration of a graphical user interface (GUI) including a real-time two-dimensional image of the heart chamber of the heart generally referenced 400, and a previously acquired three-dimensional image of the heart chamber, generally referenced 450, at a stage prior to registration of an MPS with an image detector detecting the three-dimensional image. FIG. 4B is a schematic illustration of the GUI of FIG. 4A, during registration of the MPS with the image detector. FIG. 4C is a schematic illustration of the GUI of FIG. 4A, during navigation of a probe catheter within the heart chamber. FIG. 4D is a schematic illustration of the GUI of FIG. 4C, during further navigation of the probe catheter of FIG. 4C, to another known point on the inner heart chamber surface. FIG. 4E is a schematic illustration of the GUI of FIG. 4C, during navigation of the probe of FIG. 4C, to a further known point on the inner heart chamber surface. FIG. 4F is a schematic illustration of the GUI including a two-dimensional real-time image of the heart chamber, and a previously acquired three-dimensional image of the heart chamber, including an electrophysiological map of the heart chamber, constructed and operative according to a further embodiment of the disclosed technique. FIG. 4G is a schematic illustration of the GUI of FIG. 4F, during ablation of a region of a pulmonary vein of the heart of the patient. FIG. 4H is a schematic illustration of the GUI of FIG. 4F, during ablation of another region of the pulmonary vein of the heart. FIG. 4I is a schematic illustration of a GUI including a previously acquired two-dimensional image of the heart chamber, and a previously acquired three-dimensional image of the heart chamber, constructed and operative according to another embodiment of the disclosed technique, during navigation of the probe catheter to a known point on the inner heart chamber surface. FIG. 4K is a schematic illustration of the GUI of FIG. 4J, during navigation to another known point on the inner heart chamber surface. FIG. 4L is a schematic illustration of the GUI of FIG. 4J, during navigation to a further known point on the inner heart chamber surface.

With reference to FIG. 4A, a 2D image detector detects two-dimensional real-time image 400. A tomographic image detector detects three-dimensional image 450. The tomographic image detector detects three-dimensional image 450 prior to the medical operation on the patient. A probe catheter 402 is inserted into a left atrium 404 of the heart of the patient. Probe catheter 402 is similar to probe catheter 162 as described herein above in connection with FIG. 1B, and includes an MPS sensor (not shown), and a probe 408 at the tip thereof. An MPS (not shown) is coupled with the MPS sensor and with a processor (not shown). A heart parameter measuring unit (not shown) is coupled with probe 408 and with the processor. Furthermore, a reference catheter 403, which includes an MPS sensor, is located and attached to or contacting a portion of the heart, for example, the superior vena cava or the coronary sinus. Heart motion may therefore cause the reference catheter 403 contacting the heart to move along with the heart. Thus, the MPS sensor of reference catheter 403 may likewise move in concordance with the heart and hence the MPS sensor attached to the reference catheter 403 can provide data corresponding to the actual motion of the heart (e.g., due to the cardiac and/or the respiratory cycles and/or the motion of the patient). An organ monitor (e.g., organ monitor 326 in FIG. 3) determines the activity state of the heart according to data provided by the MPS sensor. Further, when three-dimensional image 450 is acquired with the coordinate system of the image detector pre-registered with the MPS coordinate system, the situation of the three-dimensional image 450 being unaligned and/or out-of-plane with two-dimensional image 400, as depicted in FIG. 4A, may not exist and the three-dimensional image 450 may be oriented and/or aligned with the two-dimensional image 400 as shown in FIG. 4B.

With reference to FIG. 4B, the MPS is shown registered with the tomographic image detector. The MPS is similar to MPS 154 as described hereinabove in connection with FIG. 1B. A target location is marked with a first mark representation 405. This first mark representation 405 represents the target location prior to the measurement of a heart parameter.

With reference to FIG. 4C, the surgeon navigates probe catheter 402 within atrium 404, to a known point 406, by observing probe 408 in two-dimensional real-time image 400 and a representation 410 of the position of probe 408 in three-dimensional image 450. The heart parameter measuring unit determines a heart parameter (e.g., electric potential) at point 406, according to an output of probe 408. The MPS determines the position of probe 408 at point 406, according to an output of the MPS sensor. The processor associates this heart parameter with the same position. Furthermore, the processor may produce a representation of the measured heart parameters at locations in the three-dimensional image corresponding to target locations, thereby producing an electrophysiological map (not shown) of the heart according to the measured heart parameter values and the respective measurement positions. For example, processor 328 (FIG. 3) may color a three-dimensional image of the heart according to the measured heart parameters (e.g., where each color represents a voltage) at the locations in the three-dimensional image corresponding to the locations of measurement.

With reference to FIGS. 4D and 4E, the surgeon navigates probe catheter 402 to known points 412 and 414, respectively, by observing respective representations 416 and 418 of the position of probe 408, in three-dimensional image 450. The surgeon can also observe probe 408 in two-dimensional real-time image 400. The surgeon continues to navigate probe catheter 402 within the heart chamber, to additional known points sufficient for the processor to construct an electrophysiological map of the heart chamber. Each point may be marked with a second mark representation, such as mark representation 407, which represents the target location after the measurement of a heart parameter.

For example, referring to FIGS. 4C, 4D, and 4E, the heart parameter measuring unit determines the value of a heart parameter at each of points 406, 412, and 414, according to an output of probe 408, and sends data respective of these values to the processor. The MPS confirms the position of probe 408 at each of known points 406, 412, and 414, according to an output of the MPS sensor, and sends data respective of these positions to the processor. The processor associates the value of the heart parameter at each of known points 406, 412, and 414, with the respective position determined by the MPS, and in this manner constructs an electrophysiological map of the heart chamber (FIG. 4F), based on the electric potential measurements and the 3D inner surface of the cardiac chamber. With reference to FIGS. 4G and 4H, the surgeon ablates different regions of the heart chamber (e.g., around the pulmonary veins), by employing an ablating catheter 420. The points of ablation may be marked with third mark representations, such as dark circles 421, on the three-dimensional image 450.

With reference to FIGS. 4I, 4J, and 4K, the surgeon can navigate probe catheter 402 within the heart chamber, similar to the way described herein above in connection with FIGS. 4C, 4D, and 4E, except that the surgeon can observe probe 408 in a previously acquired two-dimensional image 422, instead of a two-dimensional real-time image (such as image 400 seen in FIG. 4C). Hence, in a case where a fluoroscope is used to obtain the two-dimensional image 422, the surgeon and the patient are exposed to a minimal amount of radioactive radiation. The surgeon can still observe the real-time representation of the position of probe 408, in previously acquired three-dimensional image 450.

Figure 5:
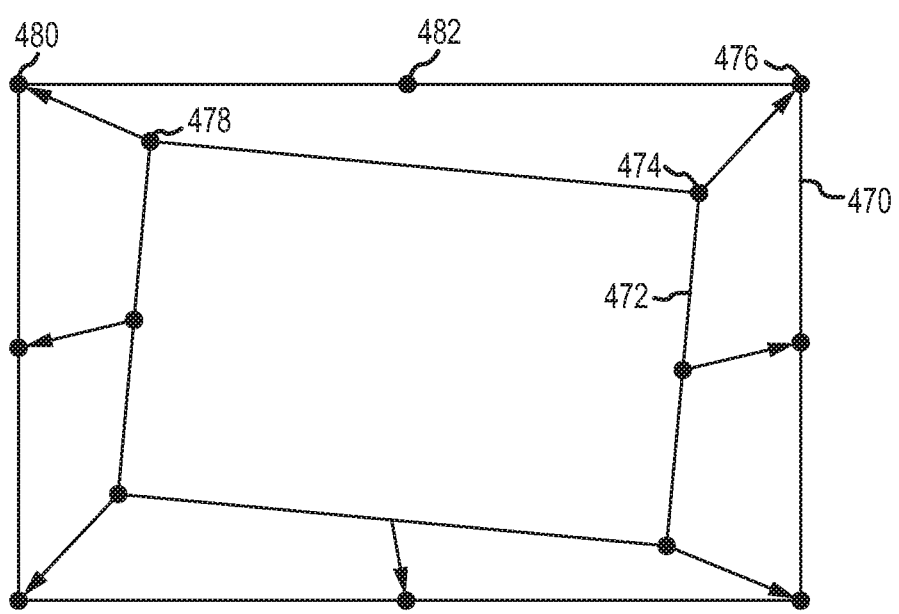
FIG. 5 is a schematic conceptual illustration of a model of the heart and the actual geometry of the heart.

As mentioned above, discrepancies may occur between the 3D image or model of the heart, displayed to the user, and the actual geometry of the heart. Thus, the position associated with a measured heart parameter may not correspond to a position of the heart in the 3D model. For example, when measuring the electric potential of the wall of the heart, the representation of the catheter in the image will not be located at the wall of the heart in the image. Consequently, the electrophysiology map of the heart may be inaccurate. To overcome the inaccuracy caused by the discrepancies between the 3D image or model of the heart and the actual geometry of the heart, either the user or a contact determining module (e.g., as described above in conjunction with FIG. 3) can determine when the tip of the catheter contacts the wall of the heart. Measurements of the heart parameter and of the position of the tip of the catheter are then acquired. A mapping or transformation may then be determined to account for the differences between the position of contact of the catheter with the wall of the heart and the correlating position of the wall of the heart in the three-dimensional image or model. A processor, such as processor 328 shown in FIG. 3, may calculate or determine the mapping or transformation. Reference is now made to FIG. 5, which is a schematic conceptual illustration of a model 470 of the heart and the actual geometry 472 of the heart. In FIG. 5, a catheter measured heart parameters at positions 474 and 478 where a physician determined that the catheter made contact with the wall of the heart. However, superimposing a representation of the value of the heart parameter measurements on model 470, at the corresponding positions thereon, would result in an erroneous electrophysiological map. Therefore, positions 474 and 478 (i.e., at which the heart parameter was measured) are mapped or transformed (e.g., by processor 328 in FIG. 3) to corresponding positions 476 and 480 in model 470 respectively. This mapping is, for example, a nearest point mapping. Alternatively, the mapping is determined according to the minimum sum of square distances. A representation of the value measured at positions 474 and 478 can be superimposed on positions 476 and 480 respectively. In case a position in model 470 is not mapped with a measurement value, an interpolated value may be calculated for the un-mapped position by using linear or non-linear interpolation techniques to approximate the un-mapped position between two mapped positions adjacent to the un-mapped position. For example, the value associated with position 482 in model 470 is determined according to an interpolation between the mapped value associated with position 476 (i.e., which was measured at position 474 in heart 472) and the mapped value associated with position 480 (i.e., which was measured at position 478 in heart 472).

Figure 6A:
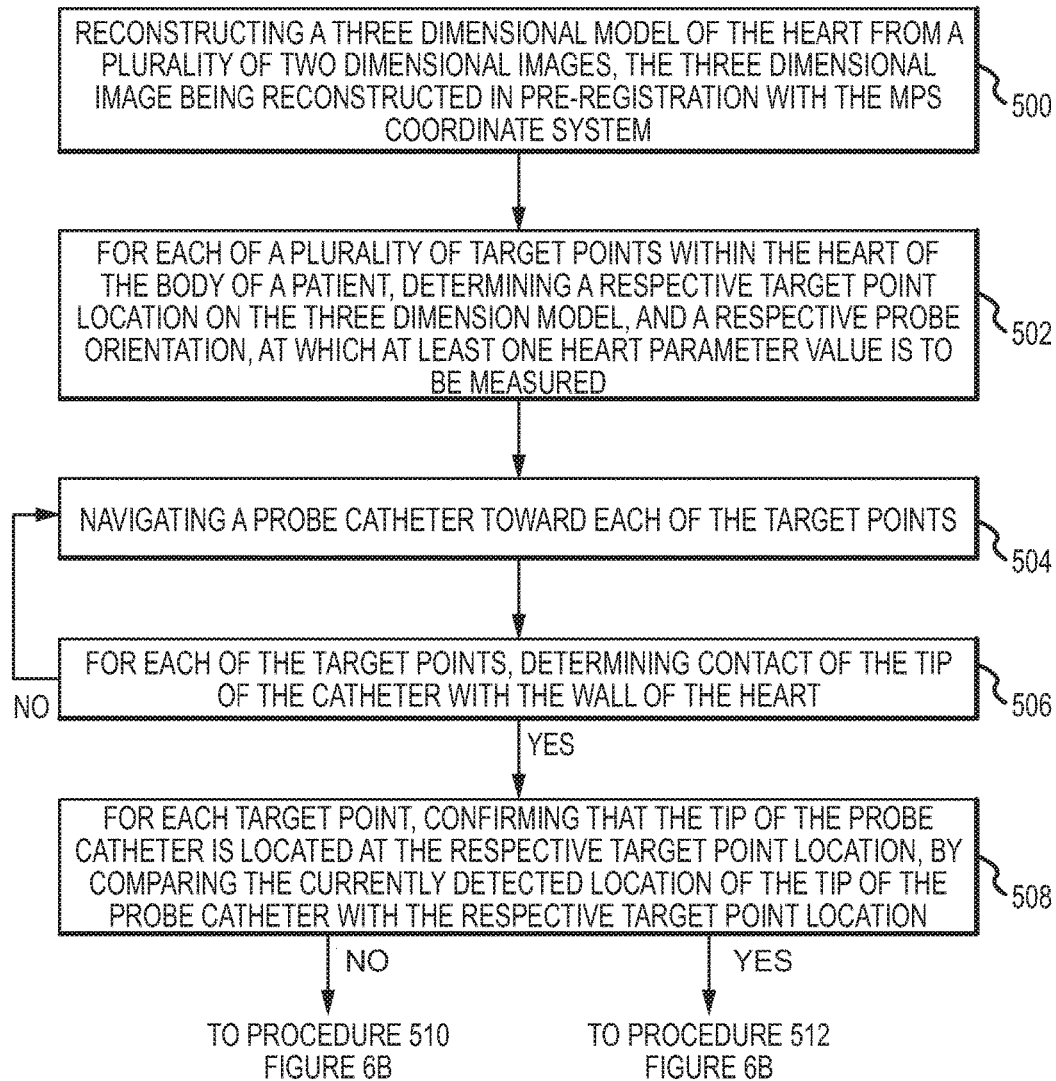
FIGS. 6A and 6B is a block diagram of an illustrative method for operating the systems of FIGS. 1A, 1B, 2 and 3, operating according to a further embodiment.
Figure 6B:
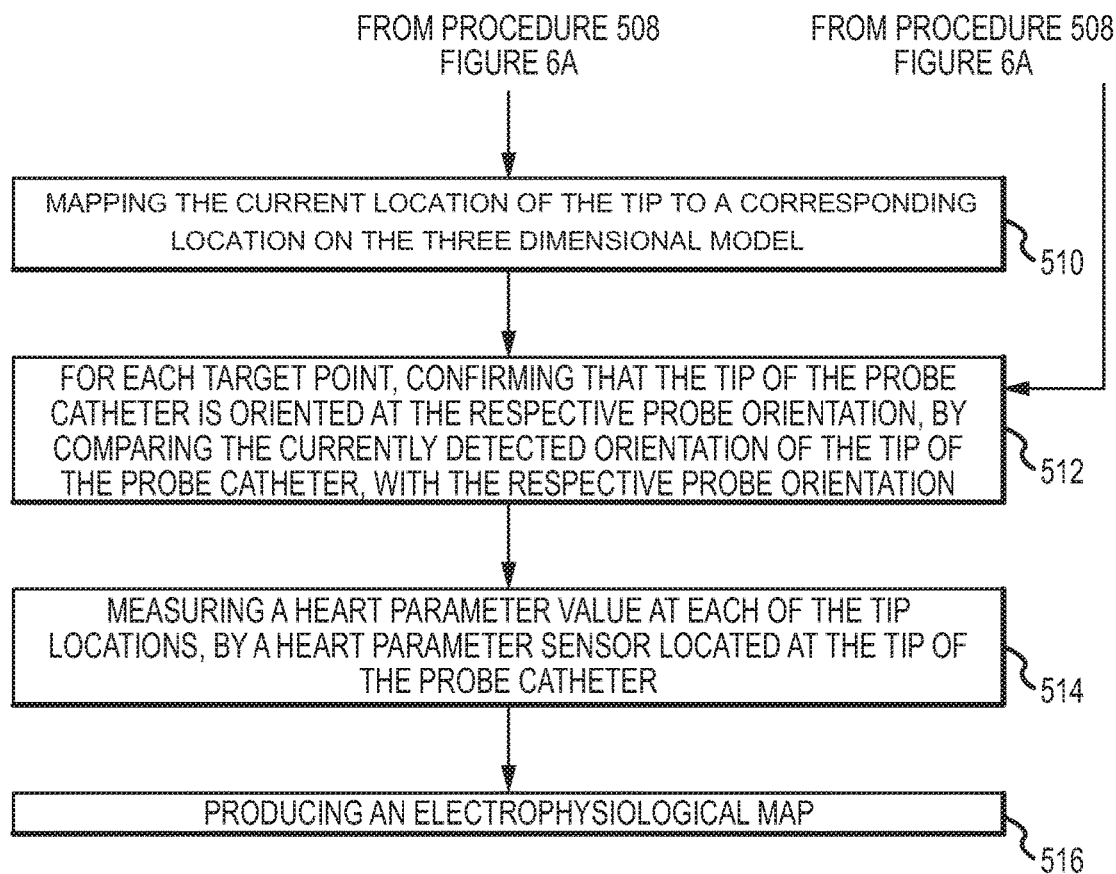

Reference is now made to FIGS. 6A and 6B, which are schematic illustrations of a method for operating the systems illustrated in FIGS. 1A, 1B, 2 and 3, operating according to a further embodiment of the disclosed technique. In procedure 500, a three-dimensional model or image of the heart is reconstructed from a plurality of two-dimensional images acquired with an image detector such as a rotational angiography or fluoroscopy system like the DynaCT system made by Siemens AG. In one embodiment, contrast dye may be injected into the left atrium. The contrast dye may be injected after the left atrium is accessed by inserting a catheter through the interatrial septum and using the catheter to inject dye into the heart. In various embodiments, the three-dimensional image may be reconstructed with the image detector coordinate system registered or pre-registered with the MPS coordinate system. The three-dimensional model may be a single three-dimensional image or a plurality of reconstructed 3D images, with each image associated with a different activity state of the heart and displayed at the corresponding real-time detected activity state. In at least one embodiment and with reference to FIG. 3, procedure 500 may include 2D image detector 318 acquiring a plurality of 2D images. Each image may be associated with a respective location in the coordinate system associated with 2D image detector 318 and with a respective activity state, determined according to an organ timing signal reading. The organ timing signal reading may be acquired by organ timing signal monitor 326. Processor 328 can group the 2D images exhibiting substantially the same organ timing signal reading and reconstruct a 3D image of the organ for each phase of the cardiac cycle according to the group of 2D images.

FIGS. 6A and 6B is a flow diagram showing an exemplary method for operating one of the systems described herein. As indicated at block 502 for each of a plurality of target points within the heart of the body of a patient, a respective target point location on the three-dimensional model and a respective probe orientation is determined at which at least one heart parameter value is to be determined. In such a procedure and with reference to FIG. 1A, for example, processor 100 may produce a marked image 112 of the heart of the patient, in which target points 104, 106, and 108 are marked (i.e., processor 100 determines a plurality of target point locations). Processor 100, additionally, can determine an acceptable range of orientations for the tip of probe catheter 162 (FIG. 1B) to assume before sensing the respective heart parameter at each of target points 104, 106, and 108, for example.

At block 504 a probe catheter is navigated or routed toward each of the target points. The step of navigating may include determining positions of the probe catheter in the MPS coordinate system and/or mapping a route in the three-dimensional model for the probe catheter to follow. In some embodiments, and with reference to FIG. 1B, the surgeon may navigate probe catheter 162 to target point 108, for example. Alternatively, an automatic navigation system can be employed for automatically navigating probe catheter 162 to target point 108. Examples of such an automatic navigation system can be generally shown with reference to commonly assigned U.S. patent application Ser. No. 12/751, 843, now pending (the '843 application), (Publication No. US-2010-0256558-A1, published 7 Oct. 2010), and reference to commonly assigned U.S. Pat. No. 8,055,327, (the '327 patent). The '843 application and the '327 patent are both hereby incorporated by reference as though fully set forth herein.

At block 506, contact of the tip of the catheter with the wall of the heart is determined. In various embodiments, the physician may determine when the catheter contacts the wall of the heart according to one or more of the signal threshold, pressure and real-time fluoroscopic image analysis methods mentioned above, for example. Alternatively, the step of determining when the catheter contacts the wall of the heart may be achieved by detecting irregularities in the movement of the tip of the catheter (e.g., irregular deceleration of the tip of the catheter or irregular orientations of the tip of the catheter). In such an embodiment and with reference to FIG. 3, for example, processor 328 can determine when the tip 308 of catheter 306 made contact with the wall of the heart. For example, with reference to FIG. 4C, the tip of catheter 402 is shown making contact with the wall of left atrium 404. If the physician or the processor 328 (FIG. 3) determines that the tip of the catheter 402 made or is making contact with the wall of the heart, the method can proceed to block 508, discussed below. On the other hand, if the tip of the catheter 402 did not make or is not making contact with the wall of the heart, the method can return to block 504 and the probe catheter may be re-navigated or routed toward the same or another target point.

At block 508, for each target point, the tip of the probe catheter is confirmed to be located at the respective target point location by comparing the currently detected location of the tip of the probe catheter with the respective target point location. In such a procedure and with reference to FIG. 1B, for example, processor 152 may compare the current location of the tip of probe catheter 162, according to an output of MPS 154, with the target point location of target point 108, according to marked image 112 (FIG. 1A), and determine whether the current location substantially matches the target point location. If the tip of the probe catheter is not located at the respective target point location, the method proceeds to block 510, discussed below. If the tip of the probe catheter is located at the respective target point location, the method proceeds to block 512.

At block 510, the current location of the tip of the probe catheter may be mapped or transformed to a corresponding location on the three-dimensional model. As mentioned above, this mapping is, for example, a nearest point mapping. Alternatively, the mapping is determined according to the minimum sum of square distances. In such a procedure and with reference to FIG. 5, for example, the current or actual location 474 is mapped to the model location 476. In some embodiments, a processor calculates a mapping or transformation function. For example, with reference to FIG. 3, processor 328 can map the current location of the catheter distal end or tip 308, which may correspond to location 474 in FIG. 5, to a corresponding location on the three-dimensional model, which may correspond to location 476 in FIG. 5. After mapping or transforming the current MPS location of the catheter tip to a corresponding location on the three-dimensional model, as necessary or desired, the method may proceed to block 512.

At block 512, for each target point, the tip of the probe catheter is confirmed to be oriented at the respective probe orientation associated with each target point, by comparing the currently detected orientation of the tip of the probe catheter with the respective probe orientation. In such a procedure and with reference to FIG. 1B, processor 152 can compare the current probe orientation of the tip of probe catheter 162, according to the output of MPS 154, with an acceptable range of orientations for the tip of probe catheter 162, as determined in procedure 502, and the processor 152 can determine whether the current probe orientation substantially matches or lies within the acceptable range of orientations. After procedure 512, the method proceeds to block 514.

At block 514, a heart parameter value is measured at each of the target points, by a heart parameter sensor located at the tip of the probe catheter. In such a procedure and with reference to FIG. 1B, for example, heart parameter measurement unit 158 can measure the heart parameter at target point 108, according to the output of heart sensor 166. Further, in various embodiments, after the heart parameter at target point 108 has been measured, the heart parameters at other target points, such as target points 104 and 106 (FIG. 1A), may be measured by carrying out procedures 504-514 as appropriate.

At block 516, an electrophysiological map is produced. The electrophysiological map may be produced by superimposing a plurality of representations of the measured heart parameter values at the respective target point locations on an image or on the three-dimensional model of the heart. In such a procedure and with reference to FIG. 1B, for example, processor 152 can produce an electrophysiological map and superimpose representations of the measured heart parameter values on an image or a 3D model of the heart or a portion thereof.

Although various embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

It will be appreciated by persons skilled in the art that the disclosed technique is not limited to what has been particularly shown and described hereinabove. Rather the scope of the disclosed technique is defined only by the claims, which follow.

What is claimed is:

1. A method for producing an electrophysiological map of a heart, the method comprising:
reconstructing a three-dimensional model of the heart from a plurality of two-dimensional images, wherein a coordinate system of the three-dimensional model is registered with a position detector coordinate system;
for each of a plurality of target points within the heart, determining a target point location associated with the three-dimensional model and a respective target probe orientation at which a heart parameter value is to be measured, wherein a combination of the target point location and the respective target probe orientation for each of the plurality of target points is different than the combination of the other of the plurality of target points;

for each target point, confirming that a probe of a catheter is located at the target point location by comparing a currently detected location of the probe with the respective target point location;

for each target point, confirming that the probe of the catheter is oriented at the probe orientation by comparing the currently detected orientation of the probe with the respective target probe orientation;

for each target point, measuring the heart parameter value with a heart parameter sensor; and producing the electrophysiological map.

2. The method according to claim 1, wherein the coordinate system of the three-dimensional model is pre-registered with the position detector coordinate system.

3. The method according to claim 1, wherein the electrophysiological map is produced by superimposing representations of the measured heart parameter values on the three-dimensional model of the heart.

4. The method according to claim 1, wherein the electrophysiological map is produced by superimposing representations of the measured heart parameter values on an image of the heart.

5. The method according to claim 1, wherein the three-dimensional model is a three dimensional image.

6. The method according to claim 5, wherein the three-dimensional image is reconstructed from a plurality of two-dimensional images, wherein each two-dimensional image is acquired from a different position, wherein a coordinate system of each two-dimensional image is pre-registered with the position detector coordinate system.

7. The method according to claim 1, wherein the three-dimensional model is a plurality of three-dimensional images each associated with a respective activity state of the heart.

8. The method according to claim 7, further comprising displaying a reconstructed three-dimensional image that exhibits an activity state that is the same as a real-time activity state.

9. The method according to claim 1, further comprising:
navigating the probe of the catheter toward each target point;
for each target point, determining contact of the probe with the wall of the heart; and
repeating navigating when contact of the probe is not determined to have been made with the wall of the heart.

10. The method according to claim 9, further comprising mapping the current location of the probe of the catheter to a corresponding location on the three-dimensional model when the probe is not located at the selected target point but contact of the probe is determined to have been made with the wall of heart.

11. A system for producing an electrophysiological map of a heart of a patient, the system comprising:
an organ monitor configured to determine an activity state of a heart;
a position detector coupled with the organ monitor and associated with a medical positioning coordinate system configured to determine the current position of a catheter according to an output of a medical positioning sensor;

a two-dimensional image detector associated with a three-dimensional coordinate system pre-registered with the medical positioning coordinate system, the two-dimensional image detector configured to acquire a plurality of two-dimensional images and associate each two-dimensional image with a position in the three-dimensional coordinate system, a position in the medical positioning coordinate system, and the activity state of the heart;

a heart parameter measurement unit configured to measure at least one heart parameter value at a target position, each heart parameter value being associated with a position in the medical positioning coordinate system; and a processor configured to receive data and to construct a three-dimensional model of the heart according to the two-dimensional images, superimpose a representation of the current position of the catheter on the three-dimensional model, access a plurality of target locations, confirm that the catheter is positioned at a first of the plurality of target locations, measure a first heart parameter value at the first of the plurality of target locations, confirm that the catheter is positioned at a second of the plurality of target point locations, measure a second heart parameter value at the second of the plurality of target locations produce an electrophysiological map with at least the first heart parameter value and the second heart parameter value, and direct a display to display the superimposed three-dimensional model according to a real-time activity state of the heart as detected by the organ monitor, wherein the three-dimensional model is a plurality of three-dimensional images each associated with a respective activity state of the heart.

12. The system according to claim 11, wherein the processor is configured to produce the electrophysiological map by superimposing representations of the heart parameter values on an image of the heart.

13. The system according to claim 11, wherein the processor is configured to mark the target position with a first mark before the heart parameter measurement unit measures the heart parameter value.

14. The system according to claim 13, wherein the processor is configured to mark the target location with a second representation after the heart parameter measurement unit measures the heart parameter value.

15. The system according to claim 14, wherein the processor is configured to mark a point of ablation with a third representation.

16. The system according to claim 11, wherein the three-dimensional model is a three-dimensional image.

17. The system according to claim 16, wherein the processor is configured to construct the three-dimensional image from a plurality of two-dimensional images, the two-dimensional image detector configured to acquire each two-dimensional image from a different position.

18. The system according to claim 11, wherein the processor is configured to determine when the catheter has made contact with a wall of the heart and determines the position of the point of contact.

19. The system according to claim 18, wherein the processor is configured to map the position of the point of contact to a corresponding location on the three-dimensional model.

* * * * *